(12) United States Patent
Kotani

(10) Patent No.: US 9,319,568 B2
(45) Date of Patent: Apr. 19, 2016

(54) ENDOSCOPE SYSTEM AND EXTERNAL CONTROL DEVICE FOR ENDOSCOPE

(71) Applicant: FUJIFILM Corporation, Tokyo (JP)

(72) Inventor: Manabu Kotani, Toyko (JP)

(73) Assignee: FUJIFILM CORPORATION, Tokyo (JP)

( * ) Notice: Subject to any disclaimer, the term of this patent is extended or adjusted under 35 U.S.C. 154(b) by 574 days.

(21) Appl. No.: 13/631,468

(22) Filed: Sep. 28, 2012

(65) Prior Publication Data

US 2013/0083179 A1    Apr. 4, 2013

(30) Foreign Application Priority Data

Sep. 30, 2011  (JP) ................................. 2011-218563

(51) Int. Cl.
| | |
|---|---|
| *A61B 1/00* | (2006.01) |
| *H04N 5/217* | (2011.01) |
| *H04N 5/232* | (2006.01) |
| *H04N 5/225* | (2006.01) |

(52) U.S. Cl.
CPC ........... *H04N 5/217* (2013.01); *H04N 5/23203* (2013.01); *A61B 1/00009* (2013.01); *H04N 2005/2255* (2013.01)

(58) Field of Classification Search
None
See application file for complete search history.

(56) References Cited

U.S. PATENT DOCUMENTS

| | | | |
|---|---|---|---|
| 6,687,779 B1 * | 2/2004 | Sturm et al. ................... | 710/305 |
| 6,792,159 B1 | 9/2004 | Aufrichtig et al. | |
| 7,894,668 B1 * | 2/2011 | Boitano ......................... | 382/168 |
| 2004/0196364 A1 | 10/2004 | Takahashi | |
| 2004/0199834 A1 | 10/2004 | Fukae | |
| 2005/0288595 A1 * | 12/2005 | Bettesh .......................... | 600/478 |
| 2007/0002134 A1 | 1/2007 | Ishihara et al. | |
| 2008/0143826 A1 | 6/2008 | Shibasaki | |
| 2008/0177137 A1 * | 7/2008 | Matsui ...................... | A61B 1/04 600/109 |
| 2009/0213212 A1 * | 8/2009 | Nakamura ....................... | 348/65 |
| 2009/0216080 A1 * | 8/2009 | Nakamura .......... | H04N 5/23203 600/109 |
| 2009/0276683 A1 | 11/2009 | Toyoda et al. | |
| 2013/0135614 A1 * | 5/2013 | Wax et al. ...................... | 356/300 |

FOREIGN PATENT DOCUMENTS

| | | |
|---|---|---|
| EP | 1 610 485 A2 | 12/2005 |
| JP | 2002-065601 A | 3/2002 |
| JP | 2004-229006 | 8/2004 |
| JP | 2006-250824 | 9/2006 |
| JP | 2008-80007 | 4/2008 |

(Continued)

OTHER PUBLICATIONS

European Search Report dated Feb. 14, 2013.

(Continued)

*Primary Examiner* — Tracy Li
*Assistant Examiner* — Mohammad J Rahman
(74) *Attorney, Agent, or Firm* — McGinn IP Law Group PLLC

(57) ABSTRACT

In the processor device connected to the endoscope, the imaging signal transmitted in serial from an imaging chip of the endoscope is converted by an S/P converter to parallel data, and is then decoded by an 8B10B decoder. When data corruption occurs due to noise or the like during transmission of the imaging signal and normal pixel data cannot be obtained due to decode error at an 8B10B decoder, that pixel data is interpolated with pixel data of a peripheral part in an inner memory of an image processing circuit.

15 Claims, 16 Drawing Sheets

(56) References Cited

FOREIGN PATENT DOCUMENTS

| | | |
|---|---|---|
| JP | 2008-148835 | 7/2008 |
| JP | 2009-201540 A | 9/2009 |
| WO | WO 2008/059588 | 5/2008 |

OTHER PUBLICATIONS

Notification of Reason(s) for Rejection dated Oct. 7, 2013, with English translation.

* cited by examiner

ENDOSCOPE SYSTEM AND EXTERNAL CONTROL DEVICE FOR ENDOSCOPE

BACKGROUND OF THE INVENTION

1. Field of the Invention

The present invention relates to an endoscope system and endoscope external control device and, in particular, to an endoscope system and endoscope external control device for serial transmission of an imaging data from a solid-state imaging element mounted at the tip of an insertion part of an endoscope to a processor device.

2. Description of the Related Art

An endoscope system is generally configured to include an endoscope having an insertion part to be inserted inside a body cavity and a hand-held operating part to be held by an operator for performing various operations and a processor device (an external control device) to be connected via a universal cable extending from the endoscope. An imaging device is mounted at the tip of the insertion part of the endoscope, and an observed image captured by the imaging device is transmitted as an imaging signal to the processor device through the insertion part and the hand-held operating part of the endoscope and a signal line passing through the inside the universal cable, and is then subjected to various image processes in the processing device and is displayed on a monitor.

Japanese Patent Application Laid-Open Nos. 2002-065601 and 2009-201540 suggest that serial transmission is used as a method of transmitting an imaging signal from the imaging device of the endoscope to the processor device. According to these gazettes, compared with the case in which an imaging signal is transmitted as an analog signal, the transmission is less prone to be influenced by noise and transmission characteristics can be improved. Also, compared with the case in which an imaging signal is transmitted as a parallel signal, the number of signal lines can be reduced (that is, the diameter of the insertion part of the endoscope can be reduced), and the transmission speed can be increased (that is, the image quality of the shot image can be increased).

Also, Japanese Patent Application Laid-Open No. 2009-201540 suggests that since the transmission distance from the imaging device of the endoscope to the processor device is long in the above-described endoscope system, if a clock signal in synchronization with the imaging signal is also transmitted from the solid-state imaging element to the processor device together with the imaging signal with application of high-speed serial transmission technology, a timing skew occurs due to a difference in parasitic capacitance and wiring resistance associated with various signal lines for each of the imaging signal and the clock signal, thereby making transmission of the imaging signal unstable and resulting in an occurrence of an erroneous data detection in the processor device to disadvantageously degrade image quality. Furthermore, Japanese Patent Application Laid-Open No. 2009-201540 suggests that the imaging signal is converted to a serial signal in the imaging device by encoding by an 8B10B encoder, embedding a clock signal in the imaging signal so that a period in a Low or High state is three clocks or less, and extracting the clock signal from the imaging signal by a clock data recovery circuit (a CDR circuit) in the processor device, thereby solving the problem of a timing skew and achieving high-speed, stabilized serial transmission of the imaging signal.

SUMMARY OF THE INVENTION

Meanwhile, when a high-frequency treatment tool is inserted in a forceps channel of the endoscope for use or when argon gas is sprayed onto an affected area from the treatment tool having a forceps channel inserted thereto for adding a high frequency as argon plasma coagulation (APC), strong noise occurs. For this reason, data corruption such as bit insertion and bit missing occurs during transmission of the imaging signal, and disturbance occurs in an image (video) obtained from the imaging signal in the processing device receiving the imaging signal, thereby disadvantageously degrading visibility when the image is displayed on a monitor.

The present invention was made in view of these circumstances described above, and has an object of providing an endoscope system in which an imaging signal is transmitted in serial from an imaging device of an endoscope to an external control device (a processor device), the endoscope system allowing reduction of disturbance of an image even if data corruption occurs due to noise or the like during transmission of the imaging signal, and the external control device for the endoscope.

To achieve the object described above, an endoscope system of the present invention includes an imaging device having a solid-state imaging element mounted at a tip of an insertion part of an endoscope, an external control device connected as an external device for the endoscope to the imaging device via a signal line and controlling the imaging device, encoding means in the imaging device, the encoding means sequentially encoding pixel data for each pixel sequentially outputted from the solid-state imaging element as an imaging signal for sequential conversion to word data for each word, imaging signal transmitting means in the imaging device, the imaging signal transmitting means converting the imaging signal obtained by the sequential conversion to word data by the encoding means from a parallel signal to a serial signal and transmitting the converted imaging signal to the external control device through the signal line, imaging signal receiving means in the external control device, the imaging signal receiving means receiving the imaging signal transmitted by the imaging signal transmitting means and sequentially converting word data sequentially received as the imaging signal from the serial signal to a parallel signal for each word, decoding means in the external control device, the decoding means sequentially decoding the word data obtained by the sequential conversion to the parallel signal by the imaging signal receiving means for each word for sequential conversion to pixel data for each pixel before the encoding is performed by the encoding means, storage means storing pixel data obtained by the sequential conversion by the decoding means, decode error detecting means in the decoding means, the decode error detecting means detecting an occurrence of a decode error indicative of a failure of the decoding, and interpolating means, when the occurrence of the decode error is detected by the decode error detecting device, interpolating pixel data of the error pixel by storing, in a memory area of the storage device where the pixel data of the error pixel is to be stored with a pixel at the time of the occurrence of the decode error being taken as an error pixel, interpolation data generated based on pixel data of one or plurality of pixels forming a peripheral part of the error pixel.

According to the present invention, when data corruption (such as bit insertion and bit missing) occurs due to noise or the like during serial transmission of the imaging signal from the imaging device to the external control device, normal pixel data cannot be obtained due to the occurrence of a decode error at the decoding means in the external control device. The pixel data at the time of the occurrence of the decode error is interpolated with pixel data (uncorrupted pixel data) of a pixel of the peripheral part. Therefore, disturbance of an image (video) obtained from the imaging signal is reduced even if data corruption occurs during the transmission of the imaging signal.

In the present invention, the storage means can be configured of one or more buffer memories storing one frame of pixel data of a plurality of pixels outputted after sequential conversion by the decoding means in units of frames as transmission units.

In the present invention, as pixel data of the one or plurality of pixels forming the peripheral part of the error pixel for generating the interpolation data, the interpolating means can use either one or plurality of pieces of pixel data among pixel data of a pixel positioned within a predetermined distance range on a same image with respect to the error pixel and pixel data of a pixel at a same position as the error pixel on an image obtained within a predetermined time range with respect to a time when the error pixel is obtained.

In the present invention, the pixel data of a pixel at a same position as the error pixel on an image obtained within a predetermined time range with respect to a time when the error pixel is obtained can comprise normal pixel data of a pixel at a same position as a position of the error pixel before or after one screen.

In the present invention, the encoding means can be an 8B10B encoder encoding pixel data of eight bits by using an 8B10B encoding scheme for conversion to word data with ten bits being taken as one word, and the decoding means can be an 8B10B decoder decoding, for each word by using the 8B10B encoding scheme, the word data obtained from the encoding by the encoding means for conversion to the pixel data of eight bits before the encoding by the 8B10B encoder.

In the present invention, the decode error detecting means can detect an occurrence of a table error and a disparity error as the decode error.

In the present invention, the imaging signal receiving means can include a clock data recovery circuit extracting a clock signal from the serial signal transmitted by the imaging signal transmitting means as the imaging signal and retiming the imaging signal with the clock signal.

In the present invention, the imaging device can include synchronous data inserting means inserting word synchronous data for word synchronization in the imaging signal to be transmitted to the external control device at predetermined intervals, and the external control device can include synchronization processing means detecting the word synchronous data in the imaging signal received from the imaging signal receiving means and, based on the detected word synchronous data, adjusting a timing of delimiting into word data for each word in the conversion by the imaging signal receiving means to the parallel signal or the conversion by the decoding means to the pixel data, to make word synchronization.

In the present invention, the solid-state imaging element of the imaging device can be a CMOS-type solid-state imaging element.

Also, an external control device for an endoscope according to the present invention controls an imaging device of the endoscope and receives an imaging signal transmitted from the imaging device as a serial signal. The external control device for an endoscope sequentially receives word data for each word obtained by sequentially encoding, for each pixel, pixel data sequentially outputted from the imaging device as the imaging signal, and the external control device includes imaging signal receiving means receiving the imaging signal transmitted from imaging device and sequentially converting word data sequentially received as the imaging signal from the serial signal to a parallel signal for each word, decoding means sequentially decoding the word data obtained by the sequential conversion to the parallel signal by the imaging signal receiving means for each word for sequential conversion to pixel data for each pixel before the encoding, storage means storing pixel data obtained by the sequential conversion by the decoding means, decode error detecting means in the decoding means, the decode error detecting means detecting an occurrence of a decode error indicative of a failure of the decoding, and interpolating means, when the occurrence of the decode error is detected by the decode error detecting means, interpolating pixel data of the error pixel by storing, in a memory area of the storage means where the pixel data of the error pixel is to be stored with a pixel at the time of the occurrence of the decode error being taken as an error pixel, interpolation data generated based on pixel data of one or plurality of pixels forming a peripheral part of the error pixel.

According to the present invention, when data corruption (such as bit insertion and bit missing) occurs due to noise or the like during serial transmission of the imaging signal from the imaging device to the external control device, normal pixel data cannot be obtained due to the occurrence of a decode error at the decoding means in the external control device. The pixel data at the time of the occurrence of the decode error is interpolated with pixel data (uncorrupted pixel data) of a pixel of the peripheral part. Therefore, disturbance of an image (video) obtained from the imaging signal is reduced even if data corruption occurs during the transmission of the imaging signal.

In the present invention, the storage means can be configured of one or more buffer memories storing one frame of pixel data of a plurality of pixels outputted after sequential conversion by the decoding means in units of frames as transmission units.

In the present invention, as pixel data of the one or plurality of pixels forming the peripheral part of the error pixel for generating the interpolation data, the interpolating means can use either one or plurality of pieces of pixel data among pixel data of a pixel positioned within a predetermined distance range on a same image with respect to the error pixel and pixel data of a pixel at a same position as the error pixel on an image obtained within a predetermined time range with respect to a time when the error pixel is obtained.

In the present invention, the pixel data of a pixel at a same position as the error pixel on an image obtained within a predetermined time range with respect to a time when the error pixel is obtained can comprise normal pixel data of a pixel at a same position as a position of the error pixel before or after one screen.

In the present invention, the word data transmitted from the imaging device as the imaging signal can be word data with ten bits obtained by encoding pixel data of eight bits by using an 8B10B encoding scheme being taken as one word, and the decoding means can be an 8B10B decoder decoding, for each word, by using the 8B10B encoding scheme, the word data obtained from the encoding for conversion to the pixel data of eight bits before the encoding.

In the present invention, the decode error detecting means can detect an occurrence of a table error and a disparity error as the decode error.

In the present invention, the imaging signal receiving device can include a clock data recovery circuit extracting a clock signal from the serial signal transmitted by the imaging signal transmitting device as the imaging signal and retiming the imaging signal with the clock signal.

In the present invention, word synchronous data for word synchronization is inserted at predetermined intervals in the imaging signal to be transmitted from the imaging device, and the external control device can include a synchronization processing device detecting the word synchronous data in the imaging signal received from the imaging signal receiving device and, based on the detected word synchronous data, adjusting a timing of delimiting into word data for each word for word synchronization in the conversion to the parallel signal by the imaging signal receiving device or in the conversion to the pixel data by the decoding device.

According to the present invention, in an endoscope system in which an imaging signal is transmitted in serial from an imaging device of an endoscope to an external control device (a processor device), disturbance of an image can be reduced even if data corruption occurs due to noise or the like during transmission of the imaging signal.

DETAILED DESCRIPTION OF THE PREFERRED EMBODIMENTS

Preferred embodiments of the present invention are described in detail below according to the attached drawings.

Figure 1:
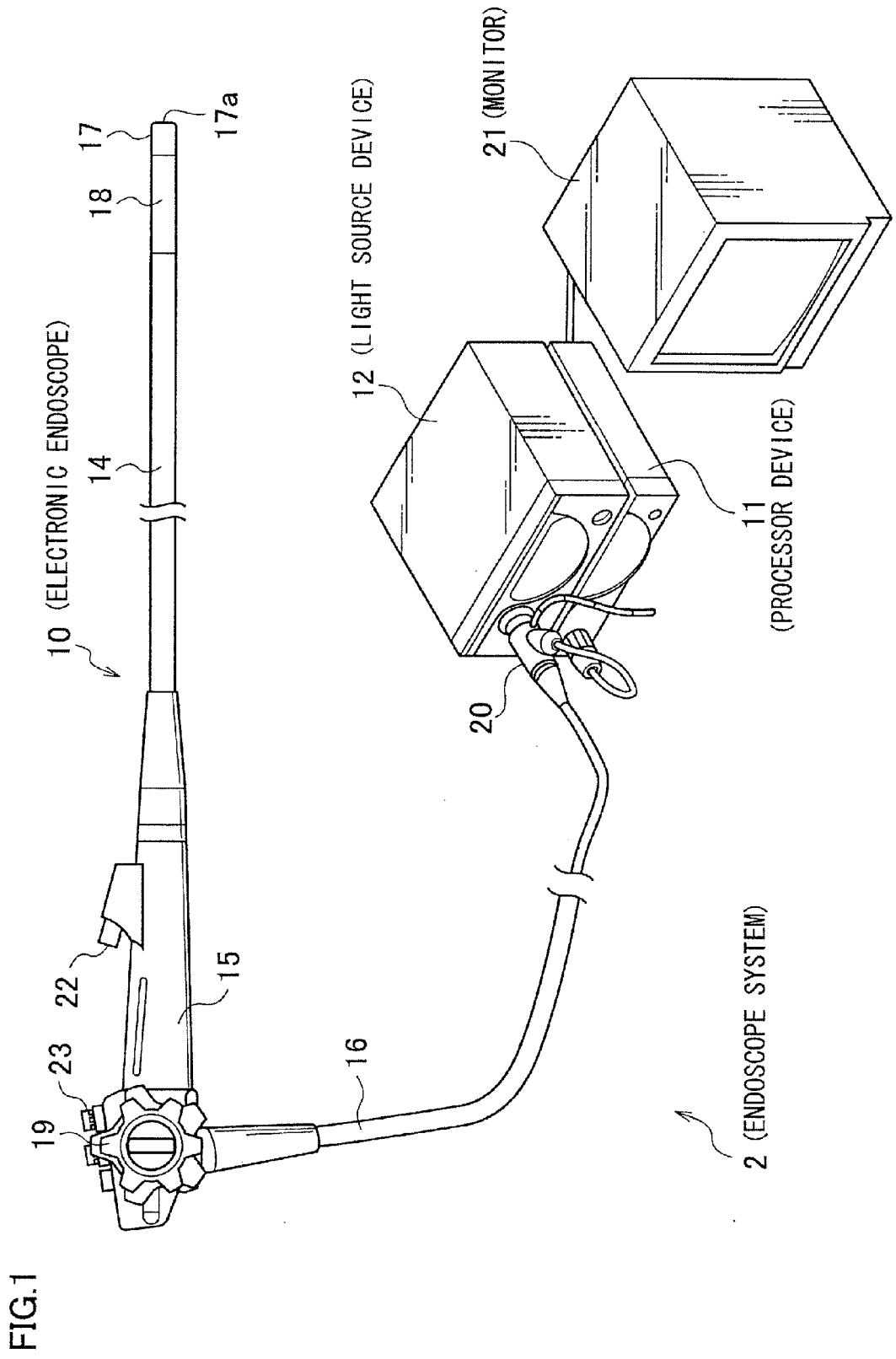
FIG. 1 is an entire view of a schematic structure of an endoscope system.

An endoscope system 2 shown in FIG. 1 is configured of an electronic endoscope 10, a processor device 11, a light source device 12, and others.

The endoscope device 10 includes a flexible insertion part 14 to be inserted inside a body cavity, an operating part 15 connected to a base end portion of the insertion part 14, and a universal cord 16 connected to the processor device 11 and the light source device 12.

At the tip of the insertion part 14, a tip part 17 having an imaging chip (an imaging device) 42 (refer to FIG. 3) for shooting an image of the inside of the body cavity incorporated therein is connected. At the rear of the tip part 17, a bendable part 18 having a plurality of bending pieces coupled to each other is provided. With an angle knob 19 provided to the operating part 15 being operated, a wire inserted in the insertion part 14 is pushed or pulled, thereby causing the bendable part 18 to perform upward, downward, leftward, and rightward bending operations. With this, the tip part 17 is oriented to a desired direction inside the body cavity.

A base end of the universal cord 16 is coupled to a connector 20. The connector 20 is of a composite type, and the processor device 11 and the light source device 12 as well are connected to the connector 20.

The processor device 11 feeds electric power to the electronic endoscope 10 via a cable 50 (refer to FIG. 3) inserted in the universal cord 16 to control the driving of the imaging chip 42, and also receives an imaging signal transmitted from the imaging chip 42 via the cable 50 and performs various signal processes on the received imaging signal for conversion to image data. The image data obtained through conversion at the processor device 11 is displayed on a monitor 21 cable-connected to the processor device 11 as an endoscopic image. Also, the processor device 11 is electrically connected to the light source device 12 via the connector 20 to control the operation of the endoscope system 2 in a centralized manner.

Figure 2:
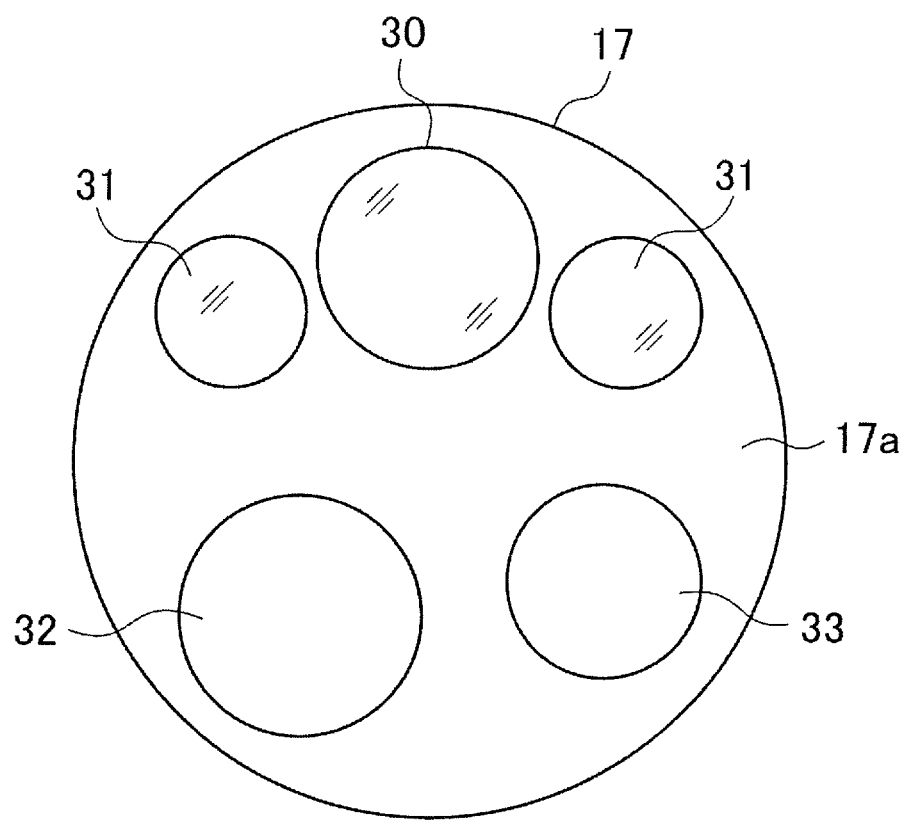
FIG. 2 is a view of a front surface of a tip of an electronic endoscope.

In FIG. 2, the tip part 17 has a front face 17a provided with an observation window 30, illumination windows 31, a forceps outlet 32, and an air-supply/water-supply nozzle 33. The observation window 30 is arranged at the center on one side of the tip part 17. Two illumination windows 31 are arranged at position symmetrical with respect to the observation window 30, emitting illumination light from the light source device 12 onto an area to be observed inside the body cavity. The forceps outlet 32 is connected to a forceps channel 51 (refer to FIG. 3) disposed inside the insertion part 14, and also communicates with a forceps port 22 (refer to FIG. 1) provided to the operating part 15. In the forceps port 22, any of various treatment tools having an injection needle, a high-frequency knife, or the like provided at its tip can be inserted, and the tip of the treatment tool is exposed from the forceps outlet 32. In response to an operation of an air-supply/water/supply button 23 (refer to FIG. 1), the air-supply/water-supply nozzle 33 injects wash water or air supplied from an air-supply/water-supply device incorporated in the light source device 12 toward the observation window 30 or the inside of the body cavity.

Figure 3:
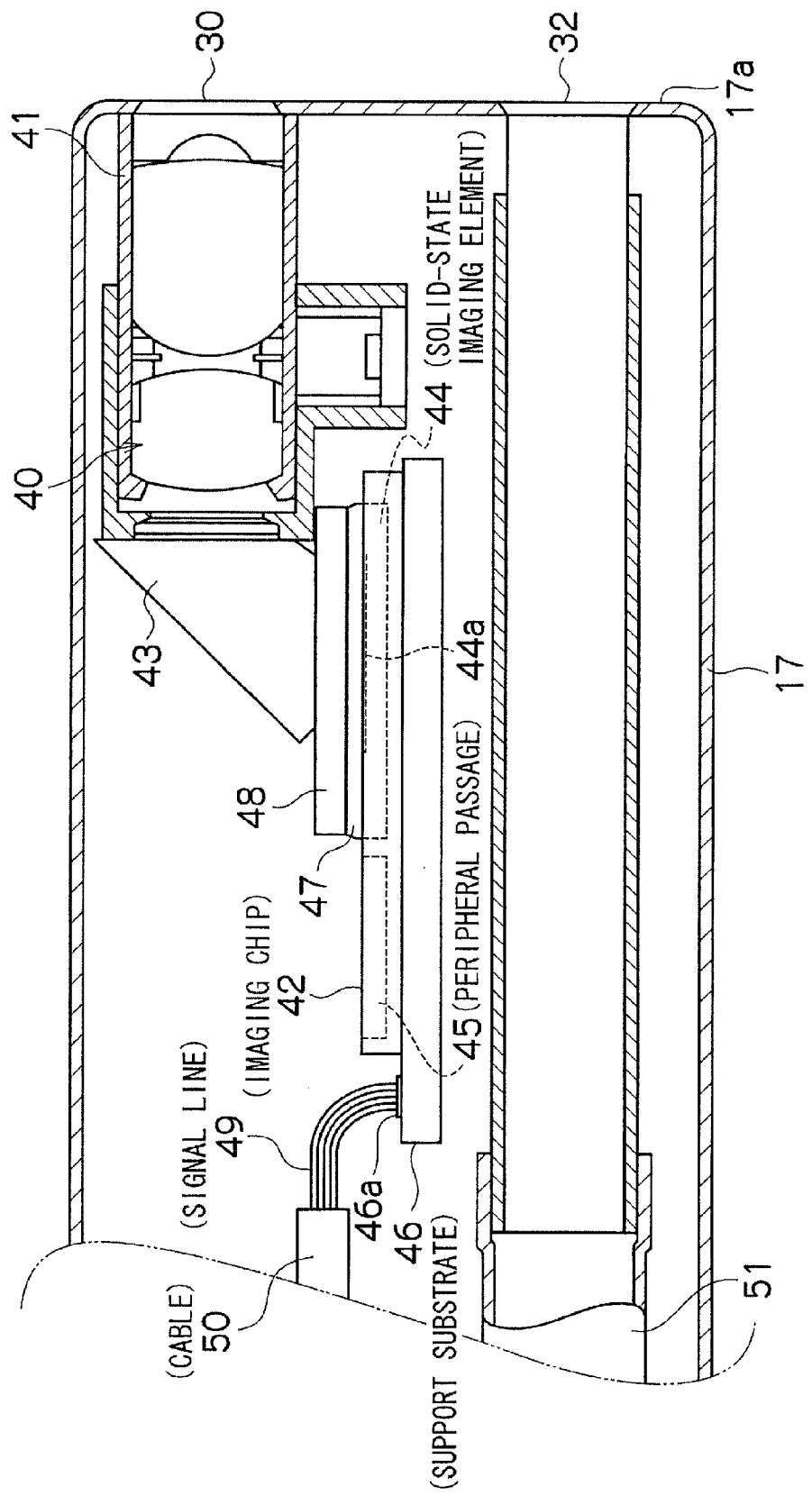
FIG. 3 is an enlarged partial sectional view of the structure of the tip of the electronic endoscope.

In FIG. 3, at the back of the observation window 30, a body tube 41 holding a objective optical system 40 for taking image light of the area to be observed inside the body cavity is arranged. The body tube 41 is mounted so that an optical axis of the objective optical system 40 is parallel to a center axis of the insertion part 14. At a back end of the body tube 41, a prism 43 is connected that guides image light of the area to be observed passing through the objective optical system 40 toward the imaging chip 42 as being bent at a substantially right angle.

The imaging chip 42 is a monolithic semiconductor (a so-called CMOS sensor chip) having a CMOS-type solid-state imaging element 44 and a peripheral circuit 45 for driving the solid-state imaging element 44 and inputting and outputting signals integrally formed therein, and is implemented on a support substrate 46. An imaging surface 44a of the solid-state imaging element 44 is arranged so as to face an outgoing plane of the prism 43. On the imaging surface 44a, a cover glass 48 shaped in a rectangular plate is mounted via a spacer 47 shaped in a rectangular frame. The imaging chip 42, the spacer 47, and the cover glass 48 are assembled with a bonding agent. With this, the imaging surface 44a is protected from entry of dust.

At a rear end of a support substrate 46 extending toward the rear end of the insertion part 14, a plurality of input/output terminals 46a are provided so as to be aligned in a width direction of the support substrate 46. To the input/output terminals 46a, signal lines 49 (signal lines 49a to 49e in FIG. 5) are connected for intermediation of exchanges of various signal with the processor device 11 via the universal cord 16. The input/output terminals 46a are electrically connected to the peripheral circuit 45 in the imaging chip 42 via a wiring, a bonding pad, and others (not shown) formed on the support substrate 46. The signal lines 49 are collectively inserted in the flexible tubular cable 50. The cable 50 is inserted in the inside of each of the insertion part 14, the operating part 15, and the universal cord 16, and is then connected to the connector 20.

Although not shown in the drawings, an illuminating part is provided at the back of the illumination windows 31. At the illuminating part, an outgoing end of a light guide guiding illumination light from the light source device 12 is provided. As with the cable 50, the light guide is inserted in the inside of each of the insertion part 14, the operating part 15, and the universal cord 16, and has an incoming end connected to the connector 20.

Figure 4:
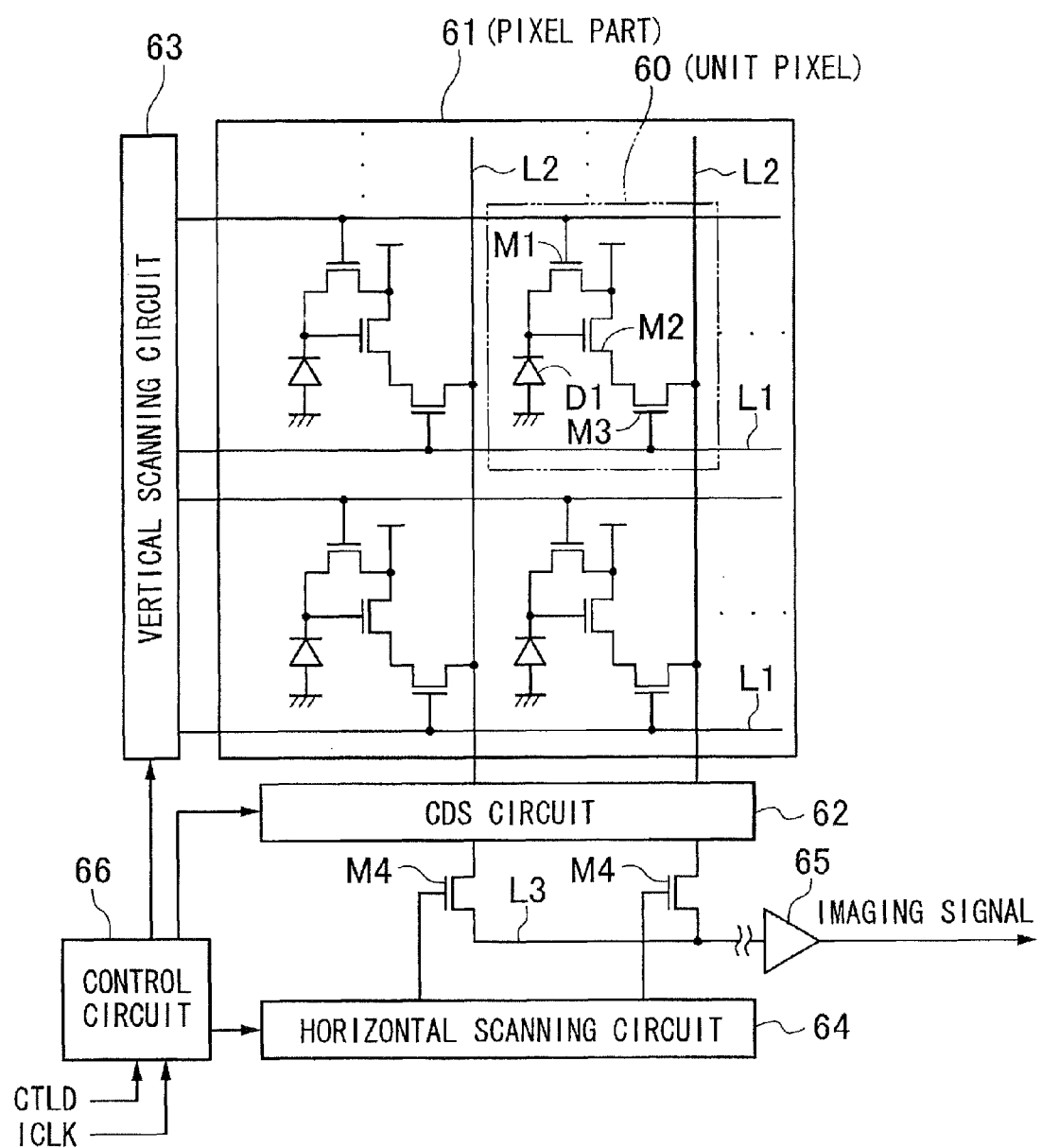
FIG. 4 is a circuit diagram of the structure of a solid-state imaging element.

In FIG. 4, the solid-state imaging element 44 is configured of a pixel part 61 having unit pixels 60 arranged in a matrix, a correlated double sampling (CDS) circuit 62 performing a process (a noise suppressing process) on an output signal (pixel data) from the pixel part 61, a vertical scanning circuit 63 controlling scanning of the pixel part 61 in a vertical direction and also controlling a reset operation of the pixel part 61, a horizontal scanning circuit 64 controlling scanning in a horizontal direction, an output circuit 65 outputting pixel data, and a control circuit 66 providing a control signal to each of the circuits 62 to 64 and controlling a timing of vertical and horizontal scanning and sampling and others.

Each unit pixel 60 is configured to include one photodiode D1, a reset transistor M1, a driving (amplifying) transistor M2, and a pixel selection transistor M3. Each unit pixel 60 is connected to a vertical scanning line (a row selection line) L1 and a horizontal scanning line (a column signal line) L2, and is sequentially scanned by the vertical scanning circuit 63 and the horizontal scanning circuit 64.

The control circuit 66 generates a control signal to be inputted to the vertical scanning circuit 63 and the horizontal scanning circuit 64 for scanning a row and a column of the pixel part 61, a control signal to be inputted to the vertical scanning circuit 63 for resetting signal charges accumulated in the photodiode D1, and a control signal to be inputted to the CDS circuit 62 for controlling connection between the pixel part 61 and the CDS circuit 62.

The CDS circuit 62 is provided as being sectioned for each column signal line L2, and sequentially outputs pixel data of each unit pixel 60 connected to the row selection line L1 selected by the vertical scanning circuit 63 according to a horizontal scanning signal outputted from the horizontal scanning circuit 64. The horizontal scanning circuit 64 controls ON/OFF of a column selection transistor M4 provided between the CDS circuit 62 and the an output bus line L3 connected to the output circuit 65 by using a horizontal scanning signal. The output circuit 65 amplifies the pixel data sequentially transferred from the column selection transistor M4 to the output bus line L3 for output. A series of pixel data outputted from the output circuit 65 is hereinafter collectively referred to as an imaging signal.

Note that although not shown in the drawings, the solid-state imaging element 44 is a solid-state imaging element of a single-plate color imaging type including a color filter (for example, primary-colors filter in a Bayer array) formed of a plurality of color segments.

Figure 5:
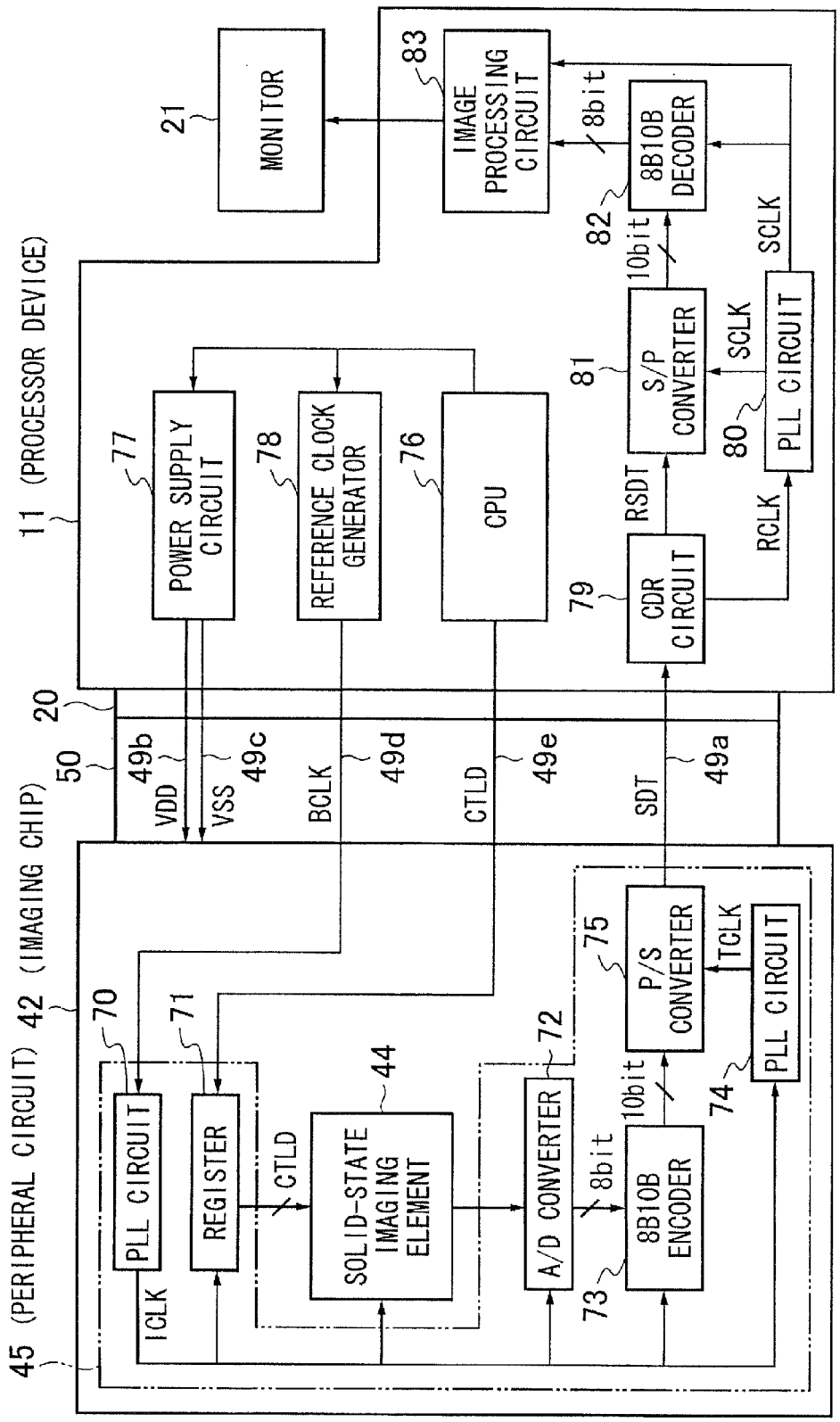
FIG. 5 is a block diagram of the structure of a solid-state chip and a processor device.

In FIG. 5, the peripheral circuit 45 in the imaging chip 42 is configured of a PLL (Phase-Locked Loop) circuit 70 generating an internal clock signal, a register setting control data to the solid-state imaging element 44, an analog-digital (A/D) converter 72 digitalizing the imaging signal outputted from the solid-state imaging element 44, an 8B10B encoder 73 performing 8B10B encoding on the digitalized imaging signal, a PLL circuit 74 generating a serial transmission clock signal, and a parallel-serial (P/S) converter 75 converting the encoded imaging signal to a serial signal for output.

The PLL circuit 70 is a phase synchronizing circuit including a phase comparator, a loop filter, a voltage control oscillator, and a frequency divider, generating an internal clock signal ICLK in synchronization with a stable reference clock signal BCLK inputted from the processor device 11 and having a frequency (obtained by multiplication) with a predetermined proportional relation with the frequency of the reference clock signal BCLK. This internal clock signal ICLK is supplied to each part in the peripheral circuit and the control circuit 66 of the solid-state imaging element 44 (refer to FIG. 4).

The register 71 retains control data CTLD inputted from the processor device 11 for driving the solid-state imaging element 44, and inputs the control data CTLD to the control circuit 66 of the solid-state imaging element 44 (refer to FIG. 4). The register 71 is a shift register for serial-parallel conversion, converting the control data CTLD inputted in a serial signal format to a parallel signal for input to the control circuit 66. As this control data CTLD, a pixel scanning type (all pixel scanning/interlace scanning), a pixel area to be scanned (the position of the unit pixel 60 from or at which scanning starts or ends), a shutter speed (exposure time), and others are inputted. The control circuit 66 controls each of the circuits 62 to 64 in the solid-state imaging element 44 based on the control data CTLD and the internal clock signal ICLK.

The A/D converter 72 quantizes each pixel data of the imaging signal outputted from the solid-state imaging element 44 as an analog signal for conversion to a digital signal of eight bits (256 levels of grayscale), and inputs the digital signal of eight bits obtained by conversion to the 8B10B encoder 73 by using eight wiring lines.

The 8B10B encoder 73 is an encoder of an 8B10B scheme adding data of redundant two bits to the pixel data of eight bits inputted from the A/D converter 72 for conversion (encoding) to pixel data of ten bits. Conversion from eight bits to ten bits is performed by using a conversion table defined by specifications. Here, with a data amount of ten bits being taken as one word, data of ten bits obtained by conversion for each pixel data of eight bits is assumed to be referred to as word data. This conversion is to prevent the presence of the same signal level ("0" or "1") for a predetermined period or more in serial transmission, which will be described further below. For example, when the original pixel data of eight bits is "00000000", conversion is made to ten-bit data of "1001110100" (word data for each word). When the original pixel data of eight bits is "00001111", conversion is made to word data of "0101110100".

The PLL circuit 74 has a structure similar to that of the PLL circuit 70 described above, generating a serial transmission clock signal TCLK obtained by multiplying the frequency of the internal clock signal ICLK by, for example, a factor of 10, and supplying the generated signal to the P/S converter 75.

Figure 6:
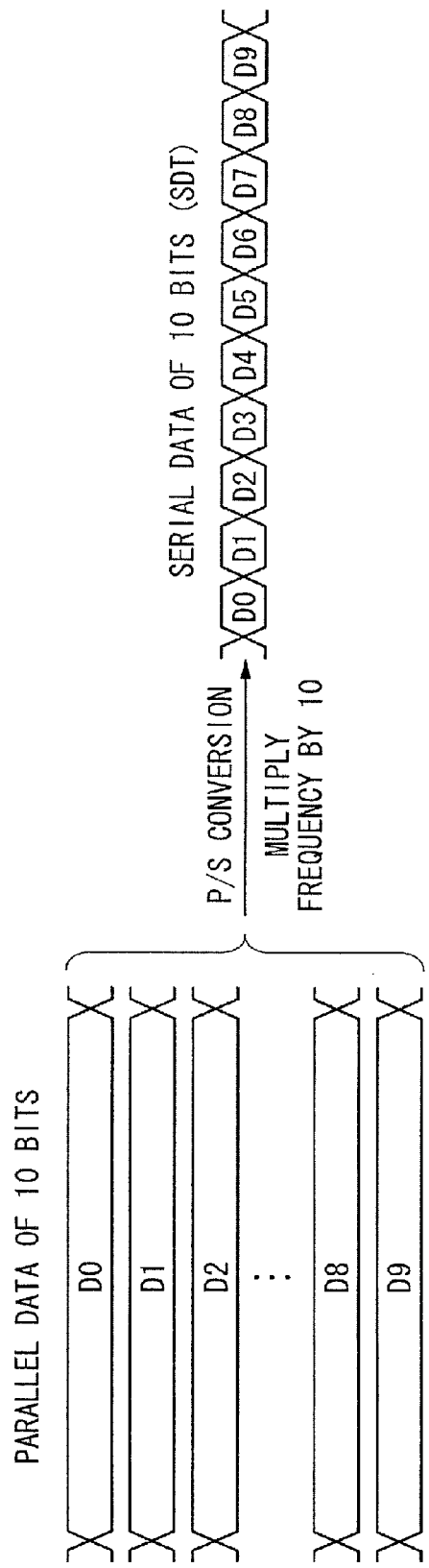
FIG. 6 is an explanatory diagram for describing parallel-serial conversion of pixel data.

The P/S converter 75 converts the pixel data (word data) sequentially inputted from the 8B10B encoder 73 from a parallel signal (parallel data) to a serial signal (serial data) according to the serial transmission clock signal TCLK generated by the PLL circuit 74 as shown in FIG. 6. Here, with the operation of the PLL circuit 74, the frequency of the serial data after conversion is ten times as large as the frequency of the parallel data before conversion. The serial data generated by the P/S converter 75 is transmitted via the signal line 49a in the cable 50 as the imaging signal SDT.

The processor device 11 is configured to include, as shown in FIG. 5, a main control circuit (CPU) 76 controlling the entire device, a power supply circuit 77 generating a power supply voltage VDD and a ground voltage VSS, a reference clock generator 78 generating the reference clock signal BCLK, a clock and data recovery (CDR) circuit 79 receiving the imaging signal SDT from the imaging chip 42 and reproducing a clock signal and a data signal from the imaging signal SDT, a PLL circuit 80 multiplying the frequency generated by the CDR circuit 79 to generate a clock signal for signal processing having the same frequency as that of the internal clock signal ICLK in the imaging chip 42, a serial-parallel (S/P) converter 81 converting a data signal (word data) generated by the CDR circuit 79 from serial data to parallel data, an 8B10B decoder 82 performing decoding of the 8B10B scheme on the word data from the S/P converter 81 to generate an imaging signal formed of pixel data of eight bits, and an image processing circuit 83 performing image processing on the decoded imaging signal to generate image data for display on the monitor 21.

The power supply circuit 77 supplies the power supply voltage VDD and the ground voltage VSS to each part in the processor device 11, and supplies these voltages to each part in the imaging chip 42 via the signal lines 49b and 49c. The reference clock generator 78 generates the reference clock signal BCLK with a stable frequency, and inputs the generated signal to the PLL circuit 70 in the imaging chip 42 via the signal line 49d.

The CPU 76 controls each parts in the processor device and generates the control data CTL described above for input to the register 71 in the imaging chip 42 via the signal line 49e.

The CDR circuit 79 detects the phase of the imaging signal SDT serially transmitted from the imaging chip 42, generates an extraction clock signal RCLK in synchronization with the frequency of this imaging signal SDT, and samples the imaging signal SDT with this extraction clock signal RCLK, thereby generating data obtained by retiming the imaging signal SDT with the extraction clock signal RCLK (retiming data: imaging signal RSDT).

Figure 7:
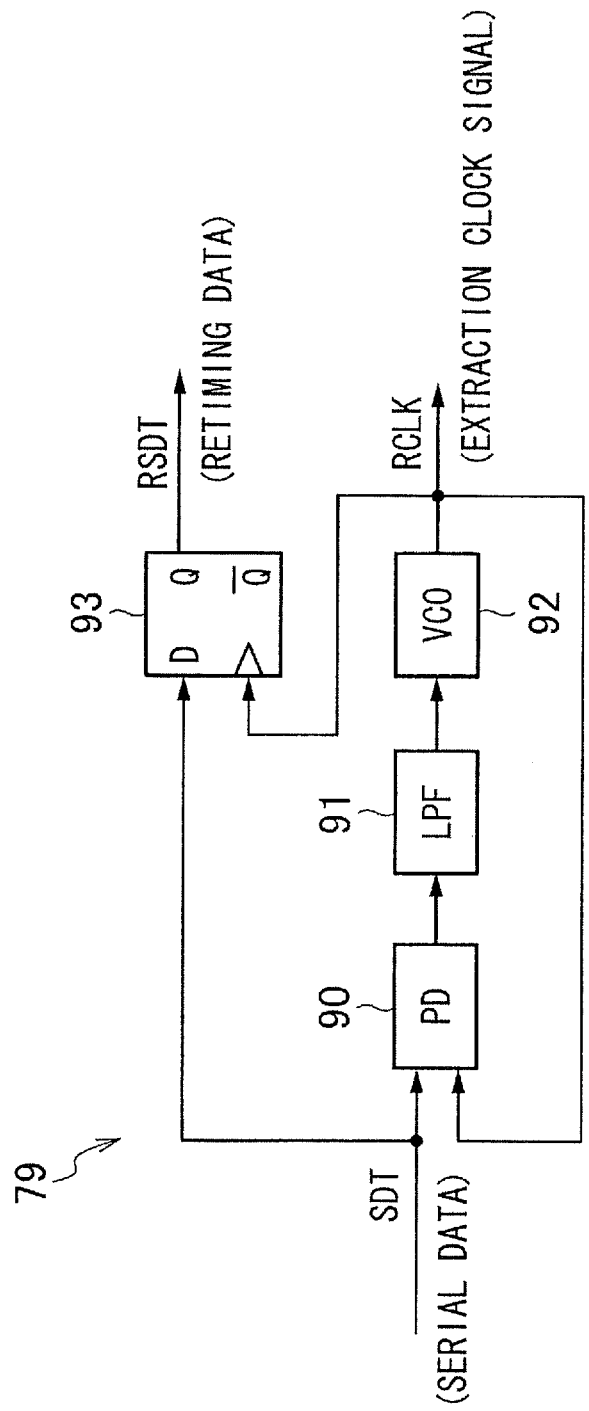
FIG. 7 is a block diagram of the structure of a CDR circuit.

Specifically, as shown in FIG. 7, the CDR circuit 79 is configured to include a phase comparator (PD) 90, a loop filter (LPF) 91, a voltage control oscillator (VCO) 92, and a D-type flip-flop 93. To the PD 90, the imaging signal SDT and the extraction clock signal RCLK generated by the VCO 92 are inputted. An output from the PD 90 is inputted to the VCO 92 via the LPF 91. The D-type flip-flop 93 has a data input terminal D to which the imaging signal SDT is inputted and a clock input terminal to which the extraction clock signal RCLK is inputted.

Figure 8:
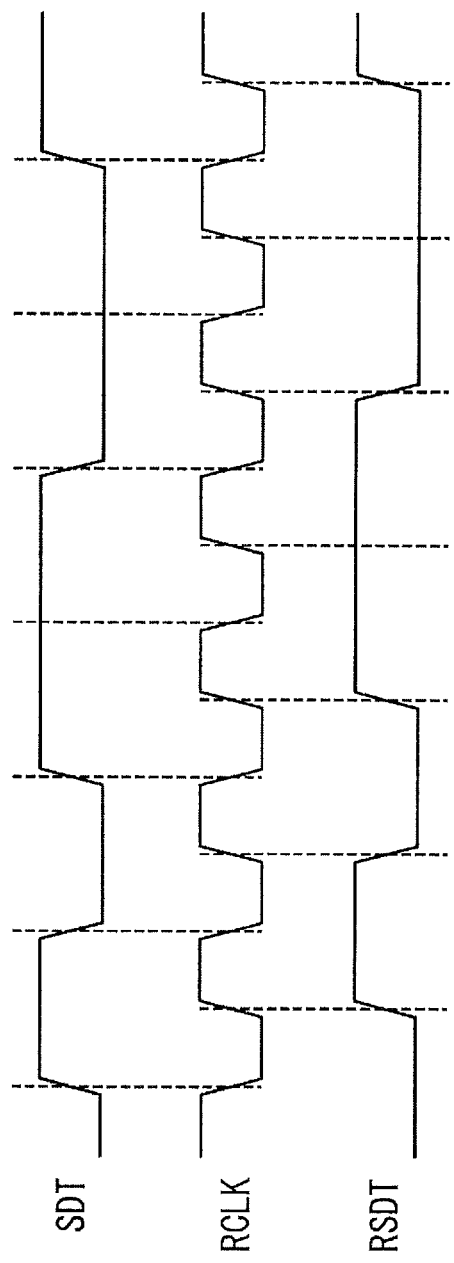
FIG. 8 is a timing chart describing the operation of the CDR circuit.

The PD 90 detects a phase difference by comparing leading edges of the imaging signal SDT and the extraction clock signal RCLK, and inputs the detection signal to the VCO 92 via the LPF 91. The VCO 92 changes the frequency of the extraction clock signal RCLK according to the inputted detection signal. As a result, as depicted in FIG. 8, the extraction clock signal RCLK in synchronization of the frequency of the imaging signal SDT is outputted from the VCO 92.

The D-type flip-flop 93 samples the imaging signal SDT with the leading edge of the extraction clock signal RCLK and retains data, reproducing the imaging signal SDT as retiming data in phase synchronization with the extraction clock signal RCLK for output from a data output terminal Q. The extraction clock signal RCLK generated by the CDR circuit 79 is inputted to the PLL circuit 80, and the reproduced imaging signal SDT is inputted to the S/P converter 81.

Referring back to FIG. 5, the PLL circuit 80 has a structure similar to that of the PLL circuit 70 describe above, multiplying the frequency of the extraction clock signal RCLK by 1/10 to generate a signal processing clock signal SCLK having the same frequency as that of the internal clock signal ICLK and supplying the generated signal to the S/P converter 81, the 8B10B decoder 82, and the image processing circuit 83.

The S/P converter 81 performs serial-parallel conversion corresponding to inverse conversion to the parallel-serial conversion shown in FIG. 6 on the imaging signal RSDT inputted from the CDR circuit 79 according to the clock signal SCLK generated by the PLL circuit 80, converting the sequentially inputted word data from serial data to parallel data. The imaging signal RSDT converted by the S/P converter 81 from serial data to parallel data for each word data is inputted to the 8B10B decoder 82.

The 8B10B decoder 82 uses a conversion table defined by the specifications of the 8B10B scheme to perform conversion (decoding) inverse to that of the 8B10B encoder 73 described above, and recovers the sequentially inputted imaging signal RSDT from parallel data of ten bits (word data) to the original parallel data of eight bits (pixel data). With this, the pixel data before encoding by the 8B10B encoder 73 can be obtained. Then, the imaging signal formed of the pixel data recovered by the 8B10B decoder 82 is inputted to the image processing circuit 83.

The image processing circuit 83 detects each pixel data contained in the imaging signal based on the clock signal SCLK and records the pixel data in an inner memory 112, and also performs image processing such as white balance adjustment, gain correction, color interpolation, contour enhancement, gamma correction, and color matrix computation to generate image data. Also, the image processing circuit 83 converts the image data to a signal format for display on the monitor 21, causing image display on the monitor 21.

When the inside of the body cavity is observed by the above-configured endoscope system 2, power supplies of the electronic endoscope 10, the processor device 11, the light source device 12, and the monitor 21 are turned ON, and the insertion part 14 of the electronic endoscope 10 is inserted in the inside of the body cavity. While the inside of the body cavity is illuminated with illumination light from the light source device 12, an image of the inside of the body cavity captured by the solid-state imaging element 44 is observed with the monitor 21.

The imaging signal generated by the solid-state imaging element 44 is converted to parallel data of eight bits by the A/D converter 72, and is encoded to parallel data of ten bits by the 8B10B encoder 73. This imaging signal formed of the parallel data of ten bits, is converted to serial data by the P/S converter 75, and is then transmitted to the processor device 11 via the signal line 49a.

The processor device 11 receives the serially transmitted imaging signal at the CDR circuit 79. The CDR circuit 79 generates a clock signal (the extraction clock signal RCLK) and a data signal in phase synchronization with this clock signal (the retiming data RSDT). The imaging signal RSDT generated as retiming data by the CDR circuit 79 is subjected to conversion by the S/P converter 81 and the 8B10B decoder 82 based on the extraction clock signal RCLK to be recovered to the original parallel data of eight bits. The imaging signal formed of this parallel data of eight bits is converted to image data by the image processing circuit 83, and an image is displayed on the monitor 21.

Next, transmission of the imaging signal from the imaging chip 4 to the processor device 11 in the endoscope system 2 described above is described.

Figure 9:
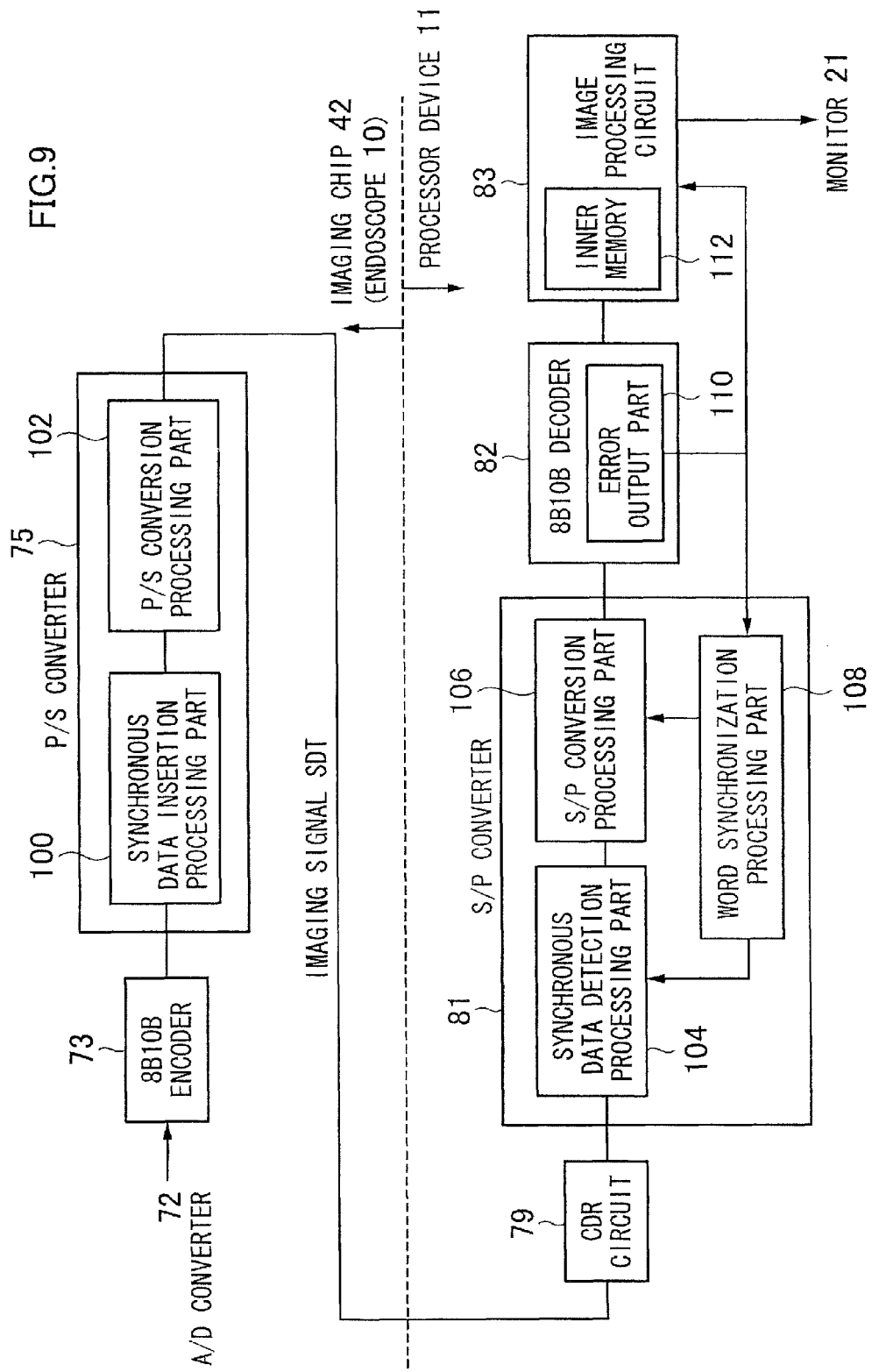
FIG. 9 is a block diagram extracting and showing the structure of a transmission system circuit related to data transmission from the imaging chip to the processor device.

FIG. 9 is a structural diagram extracting and showing a transmission system circuit of the imaging signal after the 8B10B encoder 73 shown in FIG. 5 for transmitting the pixel data from the imaging chip 42 to the processor device 11.

As described above, in the imaging chip 42, the pixel data, which is parallel data of eight bits sequentially inputted as an imaging signal, sequentially inputted from the A/D converter 72 to the 8B10B encoder 73 is converted by the 8B10B encoder 73 to parallel data of ten bits (word data with ten bits as one word), and is then inputted to the P/S converter 75. The pixel data sequentially inputted to the P/S converter 75 is converted by the P/S converter 75 from parallel data to serial data for transmission as the imaging signal SDT to the processor device 11.

At transmission of the imaging signal SDT in the imaging chip 42 as described above, word synchronous data for word synchronization is inserted in the imaging signal SDT at predetermined intervals (at predetermined time intervals and at predetermined bit intervals).

The word synchronous data is data for use in the processor device 11 receiving the serial data as the imaging signal SDT transmitted from the imaging chip 42 to check that a timing of delimiting the serial data into word data for each word is in an appropriate state as a timing of delimiting for each pixel data, that is, in the present embodiment, the word data sequentially outputted from the 8B10B encoder 73 of the imaging chip 42 and the word data sequentially obtained from the serial data in the processor device 11 receiving the serial data (the imaging signal SDT) mach each other (establish word synchronization) and to recover word synchronization if word synchronization is not established.

As this word synchronous data, word data of a bit pattern not present as output data of the 8B10B encoder 73 is used. For example, "0101111100", which is called comma data, is used as the word synchronous data. Note that the word synchronous data may have another bit pattern.

The word synchronous data is inserted in the imaging signal SDT by, for example, the P/S converter 75 of the imaging chip 42. As shown in FIG. 9, the P/S converter 75 includes a synchronous data insertion processing part 100 and a P/S conversion processing part 102.

The synchronous data insertion processing part 100 lets the word data of ten bits (one word) sequentially inputted as the imaging signal from the 8B10B encoder 73 pass through the P/S conversion processing part 102 at a later stage as shown in (A) of FIG. 10, and inserts the word synchronous data for each word between pieces of word data indicating pixel data at a predetermined timing, and outputs the result to the P/S conversion processing part 802. Note that even if the imaging signal to be inputted from the solid-state imaging element 44 to the 8B10B encoder 73 via the A/D converter 72 contains data other than the pixel data of each pixel, the data is not mentioned herein, and description is made below by assuming that only the pixel data is inputted as an imaging signal.

Figure 10:
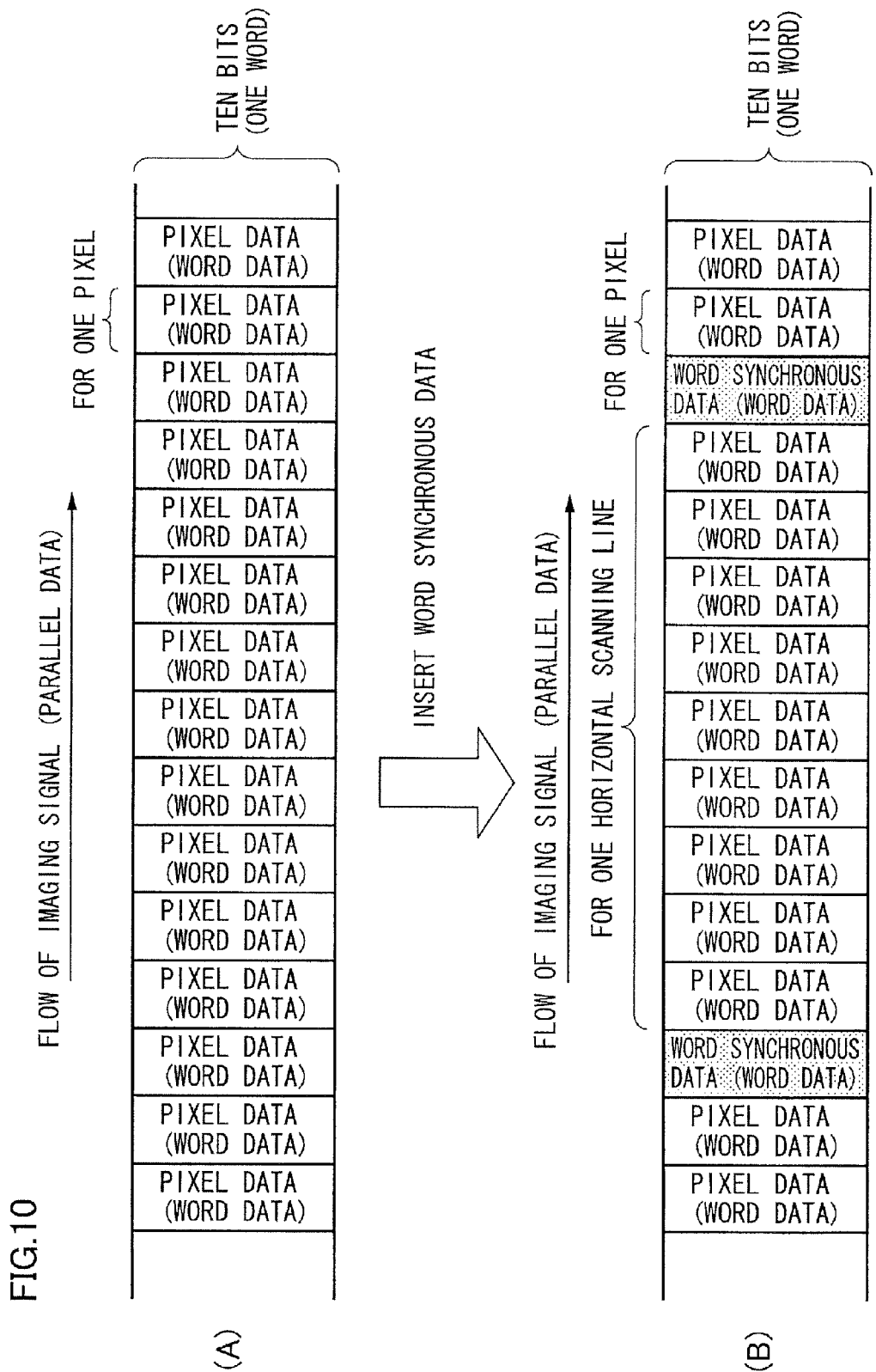
FIG. 10 is a diagram showing a data structure used for describing insertion of word synchronous data by a synchronous data insertion processing part 100 in a P/S converter.

As the timing of inserting the word synchronous data, when the pixel data is read at the solid-state imaging element 44 with a scanning scheme known as an interlace scheme or a progressive scheme, for example, as shown in (B) of FIG. 10, one piece of word synchronous data is inserted every time pixel data (word data) for one horizontal scanning line passes through the data insertion processing part 100 (that is, for each horizontal scanning period). In this case, the data insertion processing part 100 may count the number of words of the word data to be let pass therethrough and insert the word synchronous data every time word data with the number of words (the number of pixels) for one horizontal scanning line passes through. Alternatively, information about a reading position of the current pixel data may be obtained from the control circuit 66 of the solid-state imaging element 44 and the word synchronous data may be inserted based on that information. Still alternatively, as a position where the word synchronous data is to be inserted, it is possible to insert the word synchronous data before the word data of a start pixel of each horizontal scanning line or after the word data of an end pixel of each horizontal scanning line, that is, a position adjacent to word data of a specific pixel, such as a position where the horizontal scanning line of the word data to be let pass therethrough (the number of the horizontal scanning line) is switched (a position corresponding to a horizontal blanking period).

Note that the timing of inserting the word synchronous data is not necessarily for each horizontal scanning line as described above.

Figure 11:
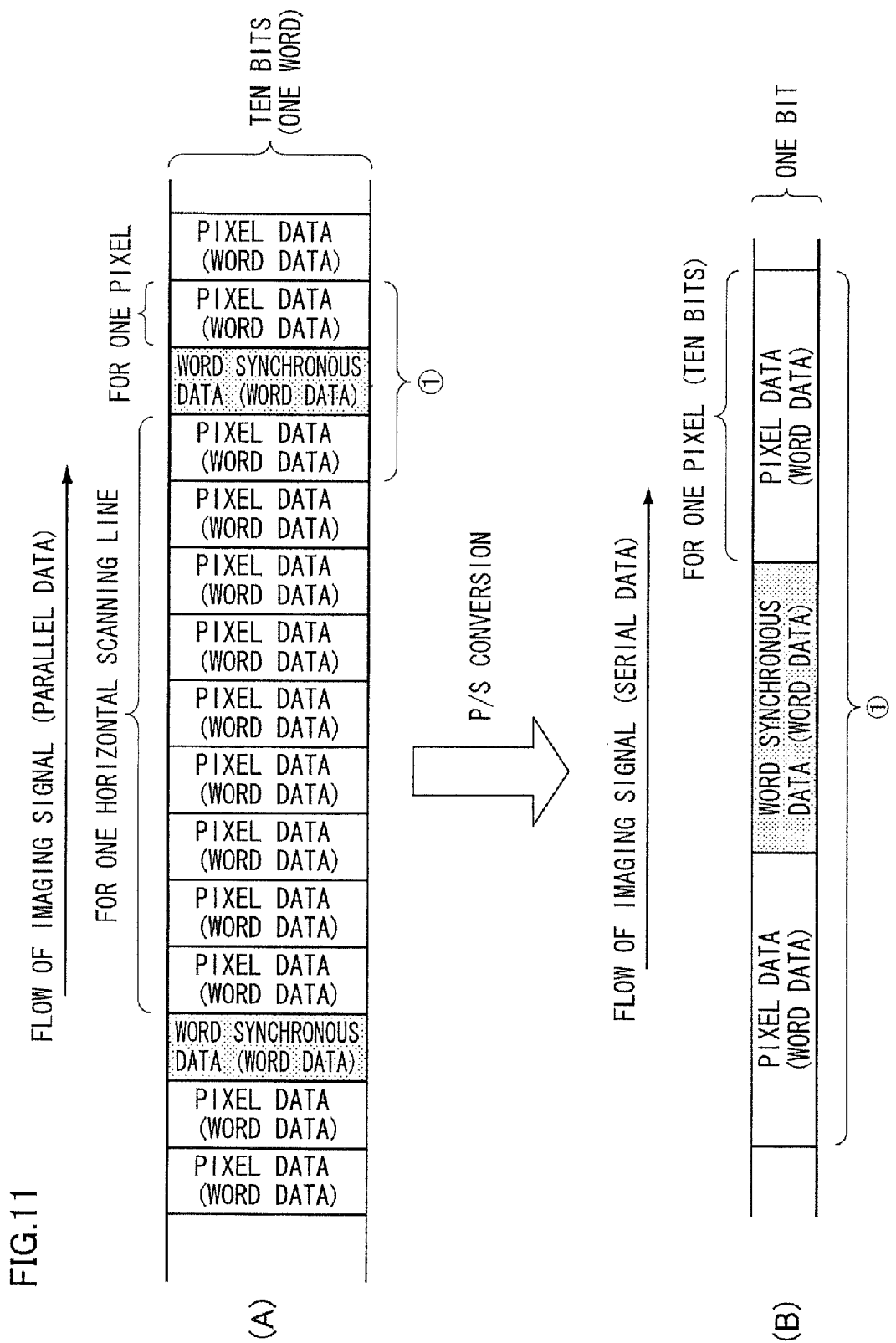
FIG. 11 is a diagram showing a data structure used for describing P/S conversion by a P/S conversion processing part in a P/S converter.

The P/S conversion processing part 102 converts the word data sequentially outputted as the imaging signal from the synchronous data insertion part 100 with the word synchronous data inserted therein as described above from parallel data to serial data as shown in FIG. 6. With this, the word data indicative pixel data having the word synchronous data inserted therein at predetermined intervals is converted from parallel data as shown in (A) of FIG. 11 to serial data as shown in (B) of FIG. 11, and the serial data having the word synchronous data inserted therein is transmitted as the imaging signal SDT from the imaging chip 42 to the processor device 11.

Figure 12:
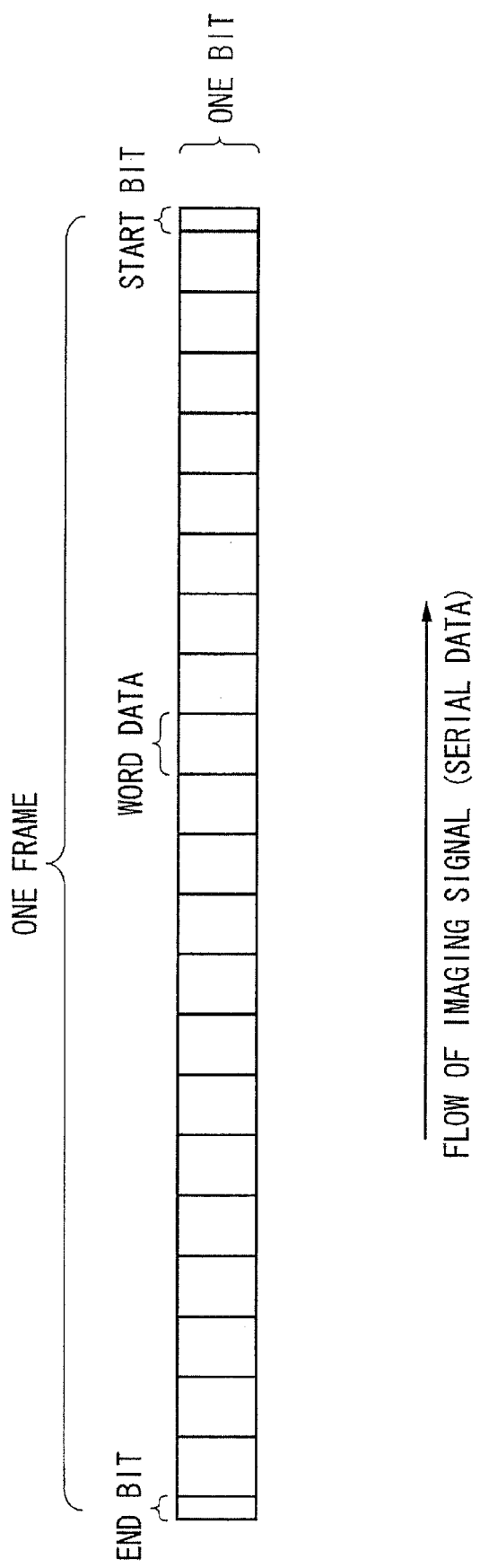
FIG. 12 is a diagram showing a data structure of an imaging signal transmitted from the imaging chip to the processor device.

Note that the P/S converter 75 transmits the imaging signal SDT with data of a predetermined number of bits as a minimum transmission unit (which is called a frame) in units of frames as shown in FIG. 12, and adds a start bit (for example, "0") indicative the start of a frame and an end bit (for example, "1") indicative the end of the frame for each frame. Also, the data amount of one frame may be, for example, a data amount when pixel data (including the word synchronous data and others) of one screen (one field in the case in which the pixel data reading scheme is an interlace scheme and one frame in the case of a progressive scheme) is transmitted in the solid-state imaging element 44, or may be a data amount when pixel data of one horizontal scanning line is transmitted. Any data amount can be set.

Also, the word synchronous data can be inserted not by the P/S converter 75 but by the 8B10B encoder or by a processing part other than the 8B10B encoder 73 and the P/S converter 75.

On the other hand, as described above, in the processor device 11, the imaging signal SDT transmitted from the imaging chip 42 is subjected to retiming by the CDR circuit 79, is then converted to parallel data of ten bits (word data) by the S/P converter 81, and is then inputted to the 8B10B decoder 82. The word data sequentially inputted to the 8B10B decoder 82 is decoded by the S/P converter 81 to the original pixel data of eight bits, and is then inputted to the image processing circuit 83.

First, a word synchronization process based on the word synchronous data at the time of receiving the imaging signal SDT in the processor device 11 described above is described. In the processor device 11, based on the word synchronous data, a process is performed to check whether word synchronization has been established and recover word synchronization when word synchronization has not been established.

Word synchronization means that, in the processor device 11 receiving the serial data transmitted from the imaging chip 42 as the imaging signal SDT, the timing of delimiting the serial data into word data for each word is set in an appropriate state as a timing of delimiting for each pixel data, that is, in the present embodiment, the word data sequentially outputted from the 8B10B encoder 73 of the imaging chip 42 and the word data sequentially outputted from the 8B10B decoder 82 of the processor device 11 match each other. If the imaging signal SDT is normally transmitted from the imaging chip 42 to the processor device 11 without data corruption (such as bit insertion or bit missing), the S/P converter 81 detects the start bit of the serial data transmitted as the imaging signal in the units of frames, and converts the following bit data string to parallel data for each word (ten bits), thereby establishing a word synchronous state.

On the other hand, during transmission of the imaging signal, particularly during transmission of the imaging signal SDT from the imaging chip 42 to the processor device 11, data corruption such as bit insertion or bit missing may occur due to an influence of noise or the like, thereby causing a deviation in timing of word synchronization and a state in which word synchronization has not been established. In this case, by checking word synchronization, it is detected that word synchronization has not been established, and the state is recovered to be such that word synchronization is established by recovering word synchronization.

The process of checking and recovering word synchronization based on the word synchronous data is performed by, for example, the S/P converter 81 of the processor device 11. As shown in FIG. 9, the S/P converter 81 includes a synchronous data detection processing part 104, an S/P conversion processing part 106, and a word synchronization processing part 108.

The synchronous data detection processing part 104 detects a bit pattern indicating the word synchronous data in the serial data sequentially inputted from the CDR circuit 79 as the imaging signal (the imaging signal RSDT subjected to retiming) and, when the word synchronous data is detected by this, provides a detection signal indicating that the word synchronous data has been detected to the word synchronization processing part 108. Also, word data other than the word synchronous data is let pass through the S/P conversion processing part 106 at a later stage, thereby removing the word synchronous data from the imaging signal. Note that the process of removing the word synchronous data from the imaging signal ma by performed in the 8B10B decoder 82 or the image processing circuit 83 at a later stage.

The S/P conversion processing part 106 delimits the word data passing through the synchronous data detection processing part 104 for each word (ten bits) for conversion from serial data to parallel data of ten bits.

Figure 13:
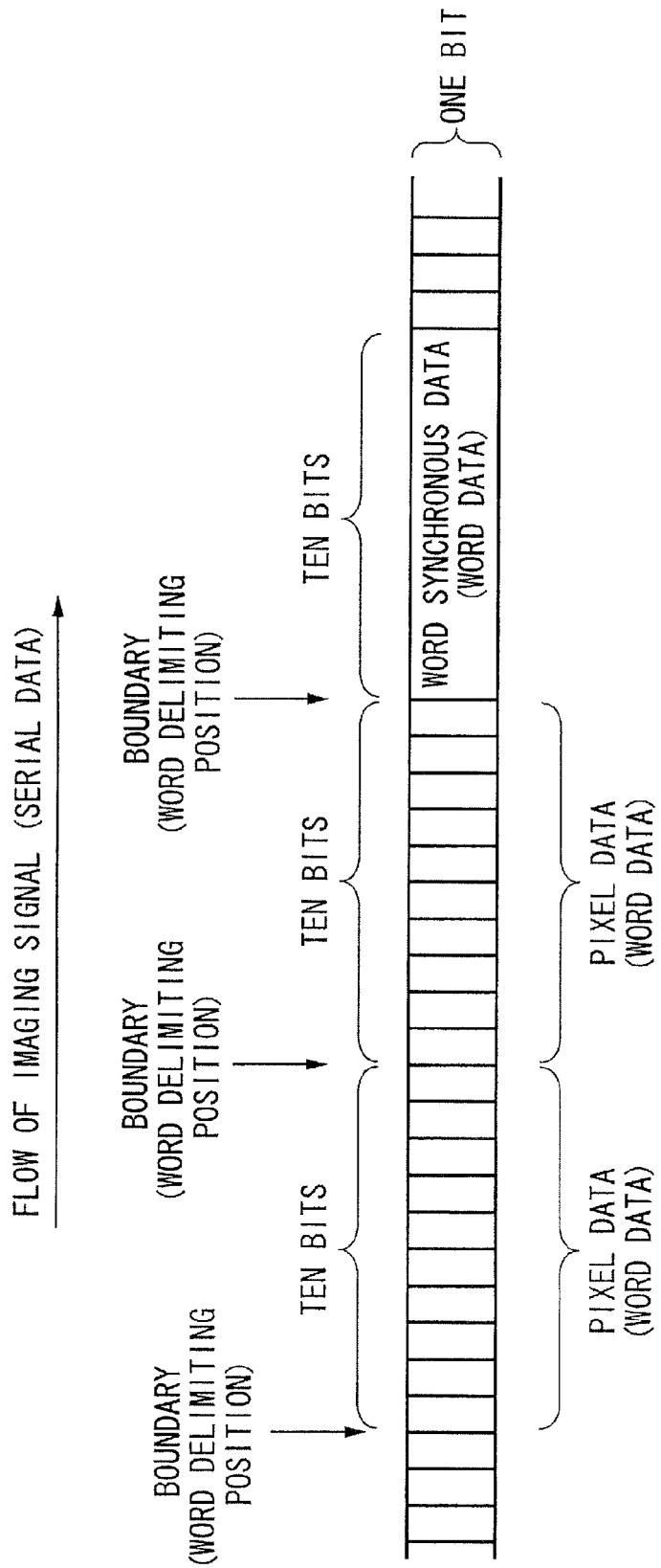
FIG. 13 is a diagram showing a data structure of an imaging signal inputted to an S/P converter.

When a detection signal indicating that the word synchronous data has been detected is provided from the synchronous data detection processing part 104 to the serial data as shown in FIG. 13 inputted from the CDR circuit 79 to the S/P converter 81 as the imaging signal, the word synchronization processing part 108 causes the S/P conversion processing part 106 to convert the serial data to parallel data of ten bits for parallel transmission as a bit data string of ten bits at a timing of delimiting a bit data string following the word synchronous data for every ten bits.

That is, at the timing of delimiting the bit data string following the word synchronous data for every ten bits (with a position where the bit data string following the word synchronous data is delimited for every ten bits being taken as a boundary of the word data (a word delimiting position)), the bit data string of ten bits is converted to parallel data of ten bits, thereby establishing a word synchronization state. However, based on the detection of the word synchronous data (a detection signal from the synchronous data detection processing part 104), the word synchronization processing part 108 adjusts the timing of S/P conversion by the S/P conversion processing part 106 converting the serial data (the bit data string) to parallel data so that word synchronization is thus established.

If the state in which word synchronization has been established is ensured when the detection signal is provided from the synchronous data detection processing part 104 to the word synchronization processing part 108, even if the timing of S/P conversion of the S/P conversion processing part 106 is adjusted, the state is not changed and, substantially, it is only confirmed that word synchronization has been established.

By contrast, if the state is such that word synchronization has not been established when the detection signal is provided from the synchronous data detection processing part 104 to the word synchronization processing part 108, the word synchronization processing part 108 adjusts the timing of S/P conversion of the S/P conversion processing part 106 based on the detection of the word synchronous data as described above, thereby recovering word synchronization.

As such, with the process of checking and recovering word synchronization (a word synchronization process) by the word synchronization processing part 108, the imaging signal converted to parallel data by the S/P conversion processing part 106 is configured of word data (pixel data) matching the imaging signal before the word synchronous data is inserted as shown in (A) of FIG. 10. That is, word synchronization (alignment) is performed so that word data inputted to the 8B10B decoder 82 at a later state with conversion from serial data to parallel data by the S/P converter 81 matches word data after the encoding by the 8B10B encoder 73. Also, during transmission of the imaging signal, even if data corruption occurs due to an influence of noise or the like to cause a deviation in word synchronization, word synchronization is recovered to an appropriate state with the word synchronization process at the word synchronization processing part 108 based on the word synchronous data.

Here, when data corruption occurs during transmission of the imaging signal or the like, data other than the word synchronous data may match a bit pattern of the word synchronous data. Here, the synchronous data detection processing part 104 erroneously the data other than the word synchronous data as word synchronous data, and if the word synchronization processing part 108 performs the word synchronization process described above based on the erroneously detected word synchronous data, the state disadvantageously becomes such as word synchronization has not been established.

To prevent this inconvenience, it is suitable to perform the word synchronization process described above (the process of checking and recovering word synchronization) based on detections of the word synchronous data a predetermined number of times (the number of times is two or more and, for example, three). That is, when the word synchronous data is detected a plurality of number of times at timings of appropriate intervals (at predetermined time intervals or bit number intervals in which the word synchronous data is inserted at the P/S converter 75), that is, timings when the word synchronous data inserted by the P/S converter 75 is to be detected, it is suitable to determine these pieces of word synchronous data as appropriate pieces of word synchronous data and perform the word synchronization process described above (the process of checking and recovering word synchronization).

As a specific mode, when word synchronous data is detected a predetermined number of times (the number of times is two or more and, for example, three) at appropriate consecutive intervals, these pieces of word synchronous data are determined as appropriate pieces of word synchronous data, and the word synchronization process described above (the process of checking and recovering word synchronization) is performed.

That is, when the detection signal indicating that word synchronous data has been detected is provided from the synchronous data detection processing part 104 to the word synchronization processing part 108 a predetermined number of times at appropriate intervals, the word synchronization processing part 108 determines that these are detection of appropriate pieces of word synchronous data. And, when detection of appropriate pieces of word synchronous data is determined, a word synchronization process is performed based on the detection signal of the latest word synchronous data detected last.

Figure 14:
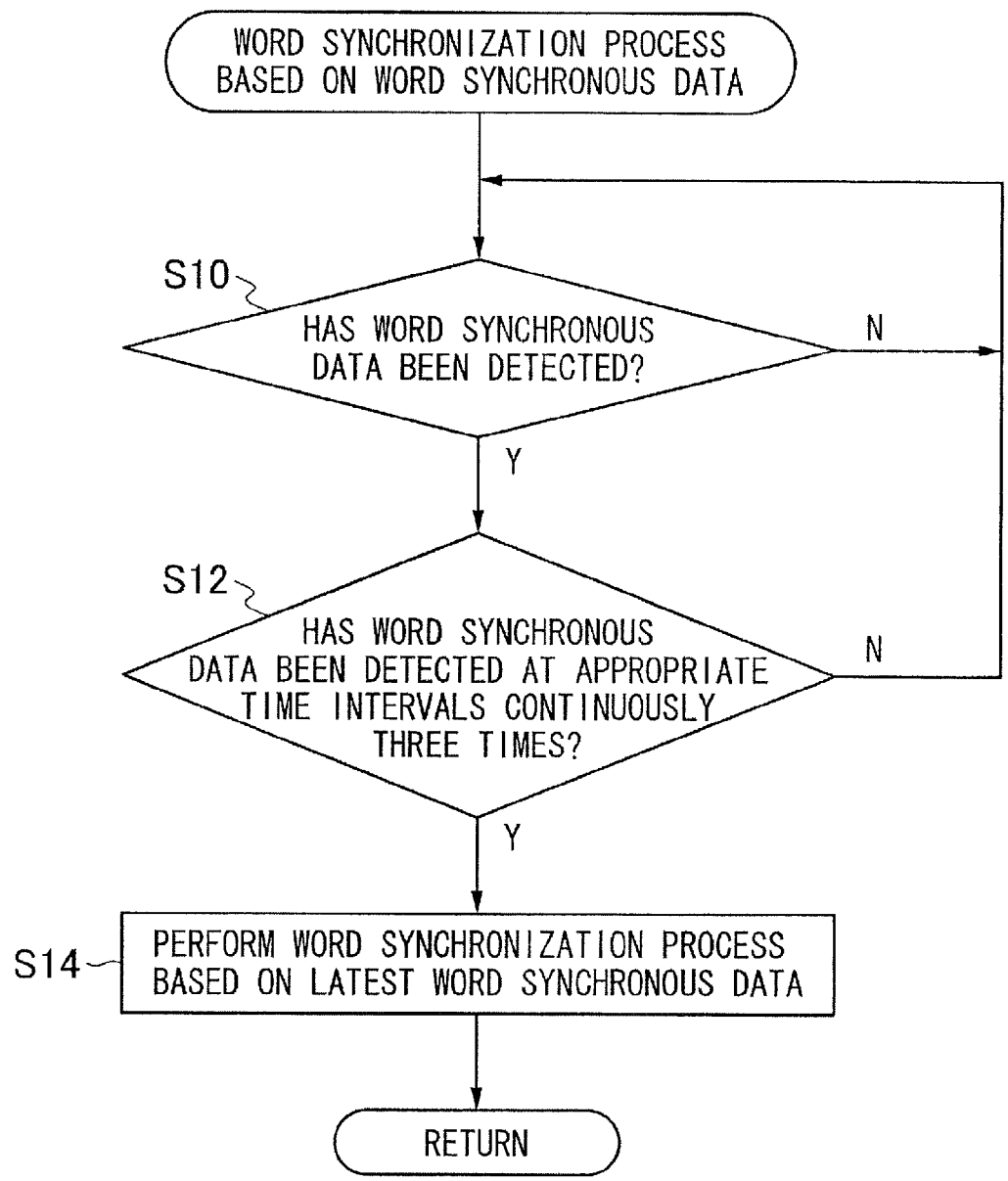
FIG. 14 is a flowchart of a process procedure of a determining process when a word synchronization processing part in the S/P converter performs a word synchronization process based on the word synchronous data.

FIG. 14 is a flowchart of a process procedure of a determining process when a word synchronization processing part 108 performs a word synchronization process based on the word synchronous data.

At step S10, it is determined whether word synchronous data has been detected. That is, it is determined whether a bit pattern matching the word synchronous data has been detected in the serial data inputted to the S/P converter 81 as the imaging signal and a detection signal has been provided from the synchronous data detection processing part 104. While No is determined in the determination process at this step S10, the process at step S10 is repeated. On the other hand, when Yes is determined, the procedure goes to step S12.

At step S12, it is determined whether the word synchronous data has been detected at appropriate time intervals continuously three times. That is, a time interval Ti (a time interval in which an appropriate piece of word synchronous data is to be detected) in which the word synchronous data is inserted is predetermined in the P/S converter 75, and it is determined at step S12 whether word synchronous data has been detected at a time T0−Ti previously back to one time interval Ti from a time T0 when word synchronous data was detected and at a time T0−2×Ti previously back to two times therefrom. When NO is determined in the determination process at this step S12, the procedure returns to the process at step S10. When YES is determined, the procedure goes to step S14. Note that while the number of times of continuation of word synchronous data is three in the present process, the number of times may not be three as long as the number is two or more. Also, in place of the appropriate time intervals, it can be determined whether word synchronous data has been detected the predetermined number of times continuously at appropriate bit number intervals (at bit number intervals where an appropriate piece of word synchronous data is to be detected, that is, the number of bits of word data to be sent between two appropriate pieces of word synchronous data).

At step S14, a word synchronization process is performed based on the latest word synchronous data detected at step S10. That is, the S/P conversion processing part 106 is caused to perform S/P conversion at a timing of delimiting the bit data string following the latest word synchronous data for each ten bits. After this process ends, the process of this flowchart ends. Note that the process of this flowchart is repeatedly performed.

According to this, even if data other than the word synchronous data is erroneously detected as word synchronous data, that detection is invalid for performing a word synchronization process, and therefore an inappropriate word synchronization process is prevented.

Also, as another mode, unlike the above case, even if an appropriate piece of word synchronous data has not been detected continuously at the predetermined number of times, if any plurality of pieces of word synchronous data among a plurality of pieces of word synchronous data to be detected at predetermined intervals in a predetermined time period have been detected, these pieces of word synchronous data may be determined as appropriate pieces of word synchronous data, and a word synchronization process may be performed. That is, if a detection signal indicating that the word synchronous data has been detected is provided from the synchronous data detection processing part 104 to the word synchronization processing part 108 at the predetermined number of times or more in the predetermined time period as matching a timing at appropriate intervals, the word synchronization processing part 108 determines that these are detection of appropriate pieces of word synchronous data. Then, when detection of appropriate pieces of word synchronous data is determined, a word synchronization process can be performed based on the detection signal of the word synchronous data detected last thereamong.

Note that detection of the word synchronous data and the process of checking and recovering word synchronization based on the word synchronous data as described above can be performed not at the S/P converter 81 but at the 8B10B decoder 82, and also can be performed at a processing part other than the S/P converter 81 and the 8B10B decoder 82. That is, in the embodiment described above, word synchronous data is detected in the serial data before inputted to the S/P conversion processing part 106 of the S/P converter 81 (before S/P conversion), and the timing of S/P conversion is adjusted based on the detected word synchronous data, thereby adjusting the timing of delimiting the serial data into word data for every ten bits to recover word synchronization. On the other hand, word synchronous data can be detected in the parallel data before inputted to the 8B10B decoder 82. Also, the process of checking and recovering word synchronization based on the word synchronous data can be performed by accumulating a plurality of words of parallel data before decoding is performed by the 8B10B decoder 82 and recreating parallel data with the timing of delimiting the serial data as word data being adjusted for decoding by the 8B10B decoder 82.

Next, a word synchronization process based on a decode error at the time of receiving the imaging signal SDT in the processor device 11 is described. In the processor device 11, a word synchronization process (a process of recovering word synchronization) is performed based on a decode error at the 8B10B decoder 82.

As a decode error, for example, there are cases in which word data inputted to the 8B10B decoder 82 is corrupted and therefore is not in the conversion table (a table error) and a running disparity is inappropriate (a disparity error).

The process regarding recovery of word synchronization based on this decode error is performed, for example, between the S/P converter 81 and the 8B10B decoder 82.

The 8B10B decoder 82 includes, as shown in FIG. 9, an error output part 110 outputting an error signal when a recovery error occurs. In the 8B10B decoder 82, when a decode error occurs at the time of decoding the imaging signal inputted from the S/P converter 81 from parallel data of ten bits (word data) to the original parallel data of eight bis (pixel data), the error output part 110 detects the occurrence of a decode error and outputs an error signal. The error signal is inputted to the word synchronization processing part 108 of the S/P converter 81 described above.

Upon the input of the error signal from the error output part 110, the word synchronization processing part 108 shifts the timing of S/P conversion at the S/P conversion processing part 106 by one bit. That is, the timing of converting serial data (a bit data string) to parallel data by the S/P conversion processing part 106 by one bit data (for delay or for advance) to shift a position where a bit data string inputted as serial data into word data (a word delimiting position shown in FIG. 13) by one bit. Then, this process is repeatedly performed until no error signal is inputted from the error output part 110, and the process described above stops when no error signal is inputted.

Figure 15:
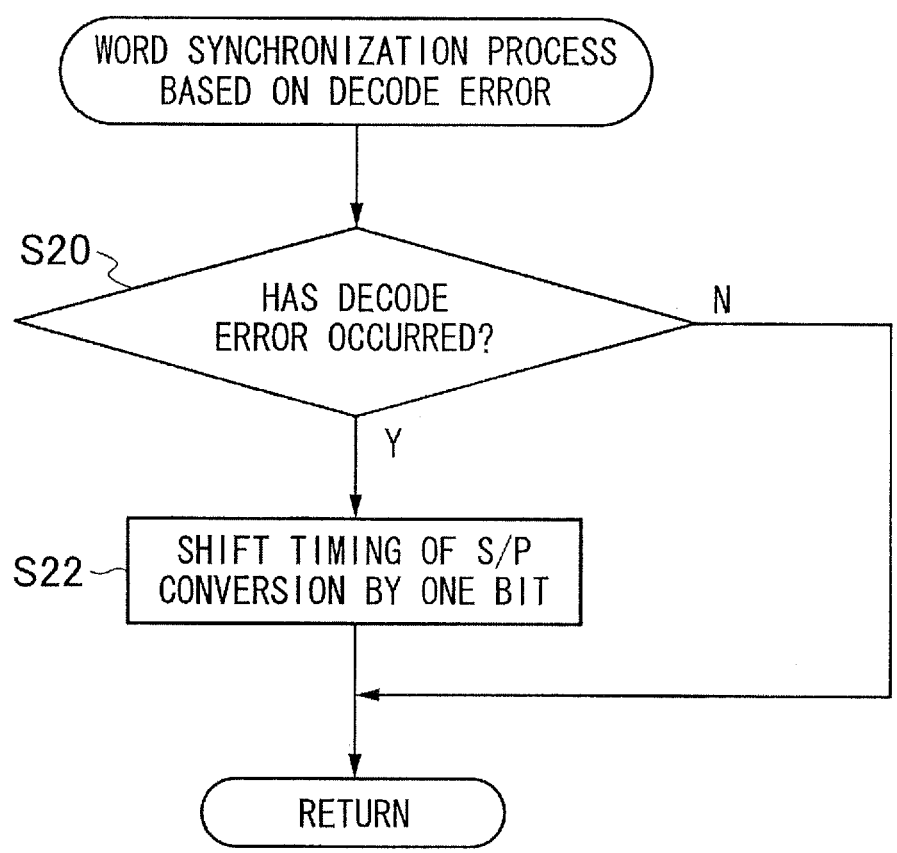
FIG. 15 is a flowchart of a process procedure when a word synchronization process is performed at the word synchronizing part in the S/P converter based on a decode error.

FIG. 15 is a flowchart of a process procedure when a word synchronization process is performed at the word synchronizing part based on a decode error of the 8B10B decoder 82.

At step S20, it is determined whether a decode error has occurred in the 8B10B decoder 82. That is, it is determined that a decode error has occurred at the 8B10B decoder 82 and an error signal has been provided from the error output part of the 8B10B decoder 82. If NO is determined in this determination process at step S20, this process of the flowchart ends. On the other hand, if YES is determined, the procedure goes to step S22. Note that since the process of this flowchart is repeatedly performed, the determination process at step S20 is repeatedly performed.

At step S22, the timing of S/P conversion at the S/P conversion processing part 106 of the S/P converter 81 by one bit. That is, the timing of converting the serial data (the bit data string) to parallel data by the S/P conversion processing part 106 is shifted by one bit of data to either an later or earlier timing than the current timing. When this process ends, the process of the flowchart ends.

According to the process shown in the flowchart, if a decode error has occurred, the process at step S22 is repeated until no decode error occurs, the timing of S/P conversion is shifted by one bit of data. In a state where no decode error occurs, the state is assumed to be such that word synchronization has been established. Therefore, when a deviation occurs in word synchronization, the process of the flowchart described above is performed to recover word synchronization.

With this, even if data corruption or the like occurs due to an influence of noise or the like during transmission of the imaging signal to cause a deviation in word synchronization, with the word synchronization process at the word synchronization processing part 108 based on the decode error, word synchronization can be recovered to be at an appropriate state. Also, it is possible to recover in a shorter period than recovery of word synchronization with the word synchronization process based on the word synchronous data, thereby achieving quick recovery.

Note that the process of recovery of word synchronization based on the decode error as described above can be performed not at the S/P converter 81 but at the 8B10B decoder 82 or at a processing part other than the S/P converter 81 and the 8B10B decoder 82. That is, in the embodiment described above, the timing of S/P conversion at the S/P conversion processing part 106 of the S/P converter 81 is changed (shifted by one bit), thereby changing the timing of delimiting the serial data into word data for every ten bits to recover word synchronization. On the other hand, as with the embodiment described above, recovery of word synchronization based on the decode error can be performed also by accumulating a plurality of words of parallel data before decoding of the 8B10B decoder 82, recreating parallel data by changing the timing of delimiting the serial data as word data (shifting by one bit), and performing decoding by the 8B10B decoder 82.

Next, a process of interpolating image data at the time of receiving the imaging signal SDT in the processor device 11 is described. In the processor device 11, when a decode error occurs in the 8B10B decoder 82, an interpolation process is performed in which pixel data at that time is interpolated with pixel data (interpolation data) generated based on pixel data of pixels of the peripheral part.

The interpolation process is performed, for example, between the 8B10B decoder 82 and the image processing circuit 83.

The image processing circuit 83 includes the inner memory (buffer memory) 112 as shown in FIG. 9. In the inner memory 112, a predetermined data amount of pixel data (for example, a data amount of pixel data for a predetermined number of screens) to be inputted to the image processing circuit 83 as an imaging signal from the 8B10B decoder 82 is accumulated. When a memory capacity of the inner memory 112 of pixel data is accumulated, the oldest pixel data is replaced with pixel data newly inputted for storage.

Figure 16:
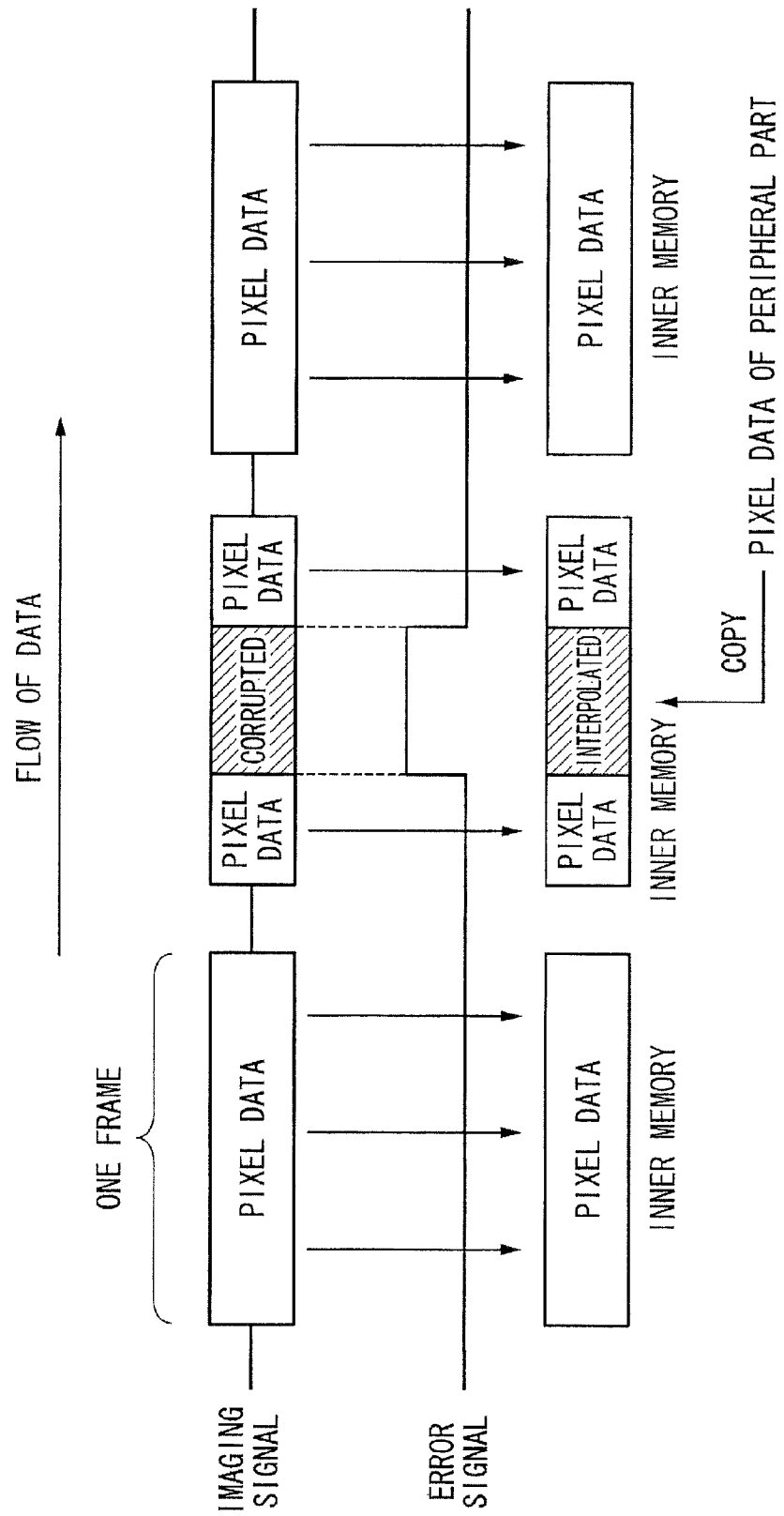
FIG. 16 is an explanatory diagram for use in describing an interpolation process in an image processing circuit.

Also, the error signal from the error output part 110 of the 8B10B decoder 82 described above is provided also to the image processing circuit 83. In the image processing circuit 83, pixel data sequentially inputted in units of frames as an imaging signal from the 8B10B decoder 82 is stored as shown in FIG. 16. Then, when an error signal is provided from the error output part 110, pixel data of a pixel (an error pixel) outputted from the 8B10B decoder 82 at this time is not stored in the inner memory 112, but interpolation data generated from pixel data of pixels of the peripheral part of the error pixel is stored in a memory area of the inner memory 112 where pixel data of the error pixel is to be stored, thereby interpolating the pixel data of the error pixel with the interpolation data.

As pixel data of the pixels forming the peripheral part of the error pixel, in addition to pixel data of pixels spatially near the error pixel, pixel data of pixels temporally near the error pixel is also included. An example of the pixel data of the pixels temporally near the error pixel is pixel data of pixels within a predetermined distance range on the same image from the error pixel. Among these, the pixel data for use in generating interpolation data may be restricted to, for example, pixel data of pixels within a predetermined distant range in a vertical direction or a lateral direction with respect to the error pixel, or to pixel data of pixels adjacent to each other with respect to the error pixel.

An example of the pixels temporally near the error pixel is pixel data of pixels at the same position with that of the error pixel on an image obtained within a predetermined time range with respect to the time of obtaining the error pixel. Among these, pixel data for use in generating interpolation data may be restricted, for example, to pixel data on an image obtained before or after one screen.

On the other hand, the interpolation data for interpolating the pixel data of the error pixel may be generated by a predetermined computing process based on pixel data of a plurality of pixels among pixels forming the peripheral part of the error pixel as described above, or may be pixel data of any one of the pixels forming the peripheral part of the error pixel.

In the former case, for example, among the pixels forming the peripheral part of the error pixel, a plurality of pixels for use in generating interpolation data are determined in advance, and an average value of pixel data of these pixels is found and taken as interpolation data. Here, the pixel data of the pixels for use in generating interpolation data may be restricted to normal pixel data (pixel data other than the error pixel). Note that the computing process for generating interpolation data based on the plurality of pieces of pixel data is not restricted to an averaging process, but another process may be used to generate interpolation data.

In the latter case, for example, among the pixels forming the peripheral part of the error pixel, one pixel for use in generating interpolation data is determined in advance, and the pixel data of this pixel is taken as interpolation data. Also in this case, normal pixel data is desirable as pixel data taken as interpolation data. Therefore, for example, it is suitable to provide a priority to each of a plurality of pixels, among the pixels forming the peripheral part of the error pixel, as pixels for use in generating interpolation data, select pixel data of pixels with the highest priority from the pixels from which normal pixel data can be obtained, take the selected pixel data as interpolation data, When an error signal is provided from the error output part 110 of the 8B10B decoder 82, the image processing circuit 83, thus generated interpolation data is stored in the inner memory 112 in place of the pixel data of the error pixel, and image data formed of the plurality of pieces of pixel data stored in the inner memory 112 is subjected to a predetermined image process, and the resultant image is displayed on the monitor 21. Therefore, even if data corruption occurs due to an influence of noise or the like during transmission of the imaging signal, disturbance in image displayed on the monitor 21 can be suppressed to minimum.

Note that the interpolation process can be performed not only by using the inner memory 112 of the image processing circuit 83 but also at a buffer memory provided between the 8B10B decoder 82 and the image processing circuit 83. For example, one or plurality of buffer memories storing pixel data for one frame, which is a transmission unit of an imaging signal, may be provided. In this case, pixel data outputted from the 8B10B decoder 82 is temporarily stored in the buffer memory (memories) in units of frames and, the buffer memory has pixel data stored therein, the pixel data of the oldest frame is outputted from the buffer memory to the image processing circuit 83, and pixel data of a new frame from the 8B10B decoder 82 is stored in that buffer memory. If a plurality of buffer memories are provided, the pixel data sequentially outputted from the 8B10B decoder 82 is cyclically stored in the plurality of buffer memories in the units of frames. In this case, the number of buffer memories is any as long as the buffer memories satisfy a capacity in which the pixel data of the pixels for use in generating interpolation data for the error pixel can be stored in the buffer memories in the state where a memory area for storing the interpolation data for the error pixel is present in each buffer memory. Also in this case, the process of reading pixel data for use in generating interpolation data from the buffer memories and generating interpolation data may be performed at the image processing circuit 83, another processing part, or a dedicatedly-provided processing part.

While the solid-state imaging element 44 is implemented by a CMOS-type solid-state imaging element in the embodiment described above, the present invention is not restricted to this, and the solid-state imaging element 44 may be implemented by a CCD-type solid-state imaging element.

Also, while pixel data of eight bits generated by the A/D converter 72 is converted by the 8B10B encoder 73 to pixel data of ten bits in the embodiment described above, the present invention is not restricted to this, and the number of bits before and after conversion can be changed as appropriate.

What is claimed is:

1. An endoscope system comprising:
an imaging device having a solid-state imaging element mounted at a tip of an insertion part of an endoscope;
an external control device connected as an external device for the endoscope to the imaging device via a signal line and controlling the imaging device;
an encoding device in the imaging device, the encoding device sequentially encoding pixel data for each pixel sequentially outputted from the solid-state imaging element as an imaging signal for sequential conversion to word data for each word;
an imaging signal transmitting device in the imaging device, the imaging signal transmitting device converting the imaging signal obtained by the sequential conversion to word data by the encoding device from a parallel signal to a serial signal and transmitting the converted imaging signal to the external control device through the signal line;
an imaging signal receiving device in the external control device, the imaging signal receiving device receiving the imaging signal transmitted by the imaging signal transmitting device and sequentially converting word data sequentially received as the imaging signal from the serial signal to a parallel signal for each word;
a decoding device in the external control device, the decoding device sequentially decoding the word data obtained by the sequential conversion to the parallel signal by the imaging signal receiving device for each word for sequential conversion to pixel data for each pixel before the encoding is performed by the encoding device;
a storage device storing pixel data obtained by the sequential conversion by the decoding device;
a decode error detecting device in the decoding device, the decode error detecting device detecting an occurrence of a decode error indicative of a failure of the decoding; and
an interpolating device, when the occurrence of the decode error is detected by the decode error detecting device, interpolating pixel data of an error pixel by storing, in a memory area of the storage device where the pixel data of the error pixel is to be stored with a pixel at a time of the occurrence of the decode error being taken as the error pixel, interpolation data generated based on pixel data of one or a plurality of pixels forming a peripheral part of the error pixel, wherein
the imaging device includes a synchronous data inserting device inserting word synchronous data into the imaging signal to be transmitted to the external control device,
the synchronous data is used to synchronize the word data, and
the external control device includes a synchronization processing device detecting the word synchronous data in the imaging signal received from the imaging signal receiving device and, based on the detected word synchronous data, adjusting a timing of delimiting into word data for each word in the conversion by the imaging signal receiving device to the parallel signal or the conversion by the decoding device to the pixel data, to make word synchronization.

2. The endoscope system according to claim 1, wherein the storage device is configured of one or more buffer memories storing one frame of pixel data of a plurality of pixels outputted after sequential conversion by the decoding device in units of frames as transmission units.

3. The endoscope system according to claim 1, wherein as pixel data of the one or plurality of pixels forming the peripheral part of the error pixel for generating the interpolation data, the interpolating device uses the either one or plurality of pieces of pixel data among pixel data of a pixel positioned within a predetermined distance range on a same image with respect to the error pixel and pixel data of a pixel at a same position as the error pixel on an image obtained within a predetermined time range with respect to a time when the error pixel is obtained.

4. The endoscope system according to claim 3, wherein pixel data of a pixel at a same position as the error pixel on an image obtained within a predetermined time range with respect to the time when the error pixel is obtained comprises normal pixel data of a pixel at a same position as a position of the error pixel before or after one screen.

5. The endoscope system according to claim 1, wherein the encoding device comprises an 8B10B encoder encoding pixel data of eight bits by using an 8B10B encoding scheme for conversion to word data with ten bits being taken as one word and the decoding device comprises an 8B10B decoder decoding for each word, by using the 8B10B encoding scheme, the word data obtained from the encoding by the encoding device for conversion to the pixel data of eight bits before the encoding by the 8B10B encoder.

6. The endoscope system according to claim 5, wherein the decode error detecting device detects an occurrence of at least one of a table error and a disparity error as the decode error.

7. The endoscope system according to claim 1, wherein the imaging signal receiving device includes a clock data recovery circuit extracting a clock signal from the serial signal transmitted by the imaging signal transmitting device as the imaging signal and retiming the imaging signal with the clock signal.

8. The endoscope system according to claim 1, wherein the solid-state imaging element of the imaging device comprises a CMOS-type solid-state imaging element.

9. An external control device for an endoscope, the external control device controlling an imaging device of the endoscope and receiving an imaging signal transmitted from the imaging device as a serial signal, the external control device sequentially receiving word data for each word obtained by sequentially encoding, for each pixel, pixel data sequentially outputted from the imaging device as the imaging signal, the external control device comprising:
an imaging signal receiving device receiving the imaging signal transmitted from the imaging device and sequentially converting word data sequentially received as the imaging signal from the serial signal to a parallel signal for each word;
a decoding device sequentially decoding the word data obtained by the sequential conversion to the parallel signal by the imaging signal receiving device for each word for sequential conversion to pixel data for each pixel before the encoding;
a storage device storing pixel data obtained by the sequential conversion by the decoding device;
a decode error detecting device in the decoding device, the decode error detecting device detecting an occurrence of a decode error indicative of a failure of the decoding; and
an interpolating device, when the occurrence of the decode error is detected by the decode error detecting device, interpolating pixel data of an error pixel by storing, in a memory area of the storage device where the pixel data of the error pixel is to be stored with a pixel at a time of the occurrence of the decode error being taken as the error pixel, interpolation data generated based on pixel data of one or plurality of pixels forming a peripheral part of the error pixel, wherein
word synchronous data is inserted into the imaging signal to be transmitted from the imaging device,
the synchronous data is used to synchronize the word data, and
the external control device includes a synchronization processing device detecting the word synchronous data in the imaging signal received from the imaging signal receiving device and, based on the detected word synchronous data, adjusting a timing of delimiting into word data for each word for word synchronization in the conversion to the parallel signal by the imaging signal receiving device or in the conversion to the pixel data by the decoding device.

10. The external control device for the endoscope according to claim 9, wherein the storage device is configured of one or more buffer memories storing one frame of pixel data of a plurality of pixels outputted after sequential conversion by the decoding device in units of frames as transmission units.

11. The external control device for the endoscope according to claim 9, wherein as pixel data of the one or plurality of pixels forming the peripheral part of the error pixel for generating the interpolation data, the interpolating device uses either one or a plurality of pieces of pixel data among pixel data of a pixel positioned within a predetermined distance range on a same image with respect to the error pixel and pixel data of a pixel at a same position as the error pixel on an image obtained within a predetermined time range with respect to a time when the error pixel is obtained.

12. The external control device for the endoscope according to claim 11, wherein pixel data of a pixel at a same position as the error pixel on, an image obtained within a predetermined time range with respect to the time when the error pixel is obtained comprises normal pixel data of a pixel at a same position as a position of the error pixel before or after one screen.

13. The external control device for the endoscope according to claim 9, wherein the word data transmitted from the imaging device as the imaging signal comprises word data with ten bits obtained by encoding pixel data of eight bits by using an 8B10B encoding scheme being taken as one word, and the decoding device comprises an 8B10B decoder decoding for each word, by using the 8B10B encoding scheme, the word data obtained from the encoding for conversion to the pixel data of eight bits before the encoding.

14. The external control device for the endoscope according to claim 13, wherein the decode error detecting device detects an occurrence of at least one of a table error and a disparity error as the decode error.

15. The external control device for the endoscope according to claim 9, wherein the imaging signal receiving device includes a clock data recovery circuit extracting a clock signal from the serial signal transmitted by the imaging signal transmitting device as the imaging signal and retiming the imaging signal with the clock signal.

* * * * *